US011992620B2

(12) United States Patent
Potenziano et al.

(10) Patent No.: US 11,992,620 B2
(45) Date of Patent: May 28, 2024

(54) METHODS OF REDUCING THE RISK OF MORTALITY ASSOCIATED WITH A MEDICAL TREATMENT

(71) Applicant: Mallinckrodt Hospital Products IP Limited, Dublin (IE)

(72) Inventors: Jim Potenziano, Binghamton, NY (US); Joe Stauffer, Skillman, NJ (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 876 days.

(21) Appl. No.: 15/854,643

(22) Filed: Dec. 26, 2017

(65) Prior Publication Data

US 2018/0185605 A1 Jul. 5, 2018

Related U.S. Application Data

(62) Division of application No. 14/313,767, filed on Jun. 24, 2014, now abandoned.

(60) Provisional application No. 61/839,352, filed on Jun. 25, 2013.

(51) Int. Cl.
*A61M 16/12* (2006.01)
*A61K 33/00* (2006.01)
*A61M 16/00* (2006.01)
*A61M 16/10* (2006.01)
*G16H 10/20* (2018.01)
*G16H 50/30* (2018.01)

(52) U.S. Cl.
CPC ............ *A61M 16/12* (2013.01); *A61K 33/00* (2013.01); *A61M 16/0096* (2013.01); *G16H 10/20* (2018.01); *G16H 50/30* (2018.01); *A61M 2016/1035* (2013.01); *A61M 2202/0208* (2013.01); *A61M 2202/025* (2013.01); *A61M 2202/0275* (2013.01); *Y02A 90/10* (2018.01)

(58) Field of Classification Search
CPC ..... A61M 16/00–0012; A61M 16/0051–0084; A61M 16/0096; A61M 16/04–0402; A61M 16/06–0666; A61M 2016/0015–0042; A61M 2016/0413; A61M 2230/00; A61M 2230/005; A61M 2230/202–205; A61M 2230/40–46; A61B 5/082–09

See application file for complete search history.

(56) References Cited

U.S. PATENT DOCUMENTS

| 5,485,827 | A | 1/1996 | Zapol et al. |
| 5,692,497 | A | 12/1997 | Schnitzer et al. |
| 5,728,705 | A | 3/1998 | Lawson et al. |
| 5,732,693 | A | 3/1998 | Bathe et al. |
| 5,846,973 | A | 12/1998 | Gehlert et al. |
| 5,890,490 | A | 4/1999 | Aylsworth et al. |
| 6,013,619 | A | * 1/2000 | Cochrane ............ C07K 14/785 514/21.3 |
| 6,259,654 | B1 | 7/2001 | De La Huerga |
| 6,390,092 | B1 | * 5/2002 | Leenhoven ....... A61M 16/0096 128/207.14 |
| 6,784,177 | B2 | 8/2004 | Cohn et al. |
| 7,114,510 | B2 | 10/2006 | Peters et al. |
| 8,282,966 | B2 | 10/2012 | Baldassarre |
| 8,293,284 | B2 | 10/2012 | Baldassarre |
| 8,431,163 | B2 | 4/2013 | Baldassarre |
| 8,795,741 | B2 | 8/2014 | Baldassarre |
| 8,846,112 | B2 | 9/2014 | Baldassarre et al. |
| 2003/0062043 | A1 | 4/2003 | Fine et al. |
| 2006/0040868 | A1 | * 2/2006 | Bowen .................. A61K 38/09 514/17.7 |
| 2008/0193566 | A1 | 8/2008 | Miller et al. |
| 2010/0130500 | A1 | 5/2010 | Kakkis |
| 2010/0256237 | A1 | 10/2010 | Auten et al. |
| 2010/0330193 | A1 | * 12/2010 | Baldassarre ........... A61K 33/00 424/600 |
| 2010/0330206 | A1 | 12/2010 | Baldassarre |
| 2011/0190611 | A1 | * 8/2011 | Rabi ................... A61M 16/125 128/207.14 |
| 2013/0068223 | A1 | 3/2013 | Baldassarre |
| 2013/0074839 | A1 | 3/2013 | Baldassarre |
| 2014/0373836 | A1 | 12/2014 | Potenziano et al. |
| 2014/0377377 | A1 | 12/2014 | Potenziano et al. |

FOREIGN PATENT DOCUMENTS

| EP | 0659445 | 6/1995 |
| EP | 0786264 | 7/1997 |
| EP | 1516639 | 3/2005 |
| WO | WO 1992/010228 | 6/1992 |
| WO | WO 1995/026768 | 10/1995 |
| WO | 2007/146311 | 12/2007 |

OTHER PUBLICATIONS

INO Therapeutics INOMAX-nitric oxide gas Highlights of Prescribing Information published 1999 (Year: 1999).*
Konduri et al., Impact of early surfactant and inhaled nitric oxide therapies on outcome in late/preterm neonates with moderate hypoxic respiratory failure Journal of Perinatology (2013) 33, 944-949 (Year: 2013).*
Ballard et al., Inhaled Nitric Oxide in Preterm Infants Undergoing Mechanical Ventilation, from The New England Journal of Medicine, vol. 355(4), Jul. 2006. (Year: 2006).*
Contemporary Pediatrics, "NICU Micropreemies: How do they fare?", Feb, 1, 2007, (https://www.contemporarypediatrics.com/view/nicu-micropreemies-how-do-they-fare-0 (Year: 2007).*

(Continued)

*Primary Examiner* — Kathryn E Ditmer
(74) *Attorney, Agent, or Firm* — Fish & Richardson P.C.

(57) ABSTRACT

Disclosed are methods of treatment that permit a reduction of risk of mortality in infants who are candidates for treatment with inhaled nitric oxide, by identifying a subset of such infants who are at an increased risk of mortality upon treatment with inhaled nitric oxide; also disclosed are related systems for use in administering inhaled nitric oxide and methods of distributing a pharmaceutical product.

5 Claims, No Drawings

(56) References Cited

OTHER PUBLICATIONS

UChicago Medicine, "Nitric Oxide can Prevent Lung Disease and Death from Premature Infants", Nov. 25, 2003, (https://www.uchicagomedicine.org/forefront/news/nitric-oxide-can-prevent-lung-disease-and-death-for-premature-infants). (Year: 2003).*
Ballard et al. NEJM 355(4): 343-353 (Year: 2006).*
INO Therapeutics, "Data Review and Bibliography: Use in Premature Neonates," 78 pages (updated Jun. 2, 2014).
Hibbs et al., "One-Year Respiratory Outcomes of Preterm Infants Enrolled in the Nitric Oxide[H1] (to Prevent) Chronic Lung Disease Trial of Inhaled Nitric Oxide," J Pediatr, 153(4):525-529 (2008).
Cole et al., "National Institutes of Health Consensus Development Conference Statement: Inhaled Nitric Oxide Therapy for Premature Infants," NIH Consens State Sci Statements, 27(5):1-34 (Oct. 27-29, 2010).
Lao et al., "Evaluating Self-declared Ancestry of U.S. Americans with Autosomal, Y-chromosomal and Mitochondrial DNA," Human Mutation in Brief, 31:E1875-E1893 (2010).
Ortega et al., "Pharmacogenetics: Implications of race and ethnicity on defining genetic profiles for personalized medicine," J Allergy Clin Immunol, 133:16-26 (2014).
The Franco-Belgium Collaborative NO Trial Group, "Early compared with delayed inhaled nitric oxide in moderately hypoxaemic neonates with respiratory failure: a randomised controlled trial," Lancet, 354:1066-1071 (1999).
Dani et al., "Inhaled nitric oxide in very preterm infants with severe respiratory distress syndrome," Acta Paediatrica, 95:1116-1123 (2006).
Field et al., "Neonatal Ventilation with Inhaled Nitric Oxide Versus Ventilatory Support Without Inhaled Nitric Oxide for Preterm Infants With Severe Respiratory Failure: The INNOVO Multicentre Randomised Controlled Trial (ISRCTN)," Pediatrics, 115:926-936 (2005).
Hascoet et al., "The Safety and Efficacy of Nitric Oxide Therapy in Premature Infants," J Pediatr, 146:318-323 (2005).
Peliowski et al., "Inhaled nitric oxide use in newborns," Paediatr Child Health, 17(2):95-97 (2012).
Macrae et al., "Inhaled nitric oxide therapy in neonates and children: reaching a European consensus," Intensive Care Med, 30:372-380 (2004).
Srisuparp et al., "Inhaled nitric oxide therapy in premature infants with mild to moderate respiratory distress syndrome," J Med Assoc Thai, 85(Suppl 2):S469-S478 (2002).
Su and Chen, "Inhaled nitric oxide in the management of preterm infants with severe respiratory failure," Journal of Perinatology, 28:112-116 (2008).
Subhedar et al., "Open randomised controlled trial of inhaled nitric oxide and early dexamethasone in high risk preterm infants," Archives of Disease in Childhood, 77:F185-F190 (1997).
Van Meurs et al., "Inhaled Nitric Oxide for Premature Infants with Severe Respiratory Failure," The New England Journal of Medicine, 353(1):13-22 (2005).
Van Meurs et al., "Inhaled nitric oxide in infants >1500 g and <34 weeks gestation with severe respiratory failure," Journal of Perinatology, 27:347-352 (2007).
Food and Drug Administration, U.S. Department of Health and Human Services, "Guidance for Industry: Collection of Race and Ethnicity Data in Clinical Trials." Sep. 2005.
Tang et al., "Genetic Structure, Self-Identified Race/Ethnicity, and Confounding in Case-Control Association Studies," Am J Hum Genet 76:268-275 (2005).
Checchia et al., "Nitric oxide delivery during cardiopulmonary bypass reduces postoperative morbidity in children—a randomized trial," J Thorac Cardiovasc Surg 146:530-536 (2013).
Minutes of U.S. Food & Drug Administration Pediatric Advisory Committee Meeting of Mar. 14, 2013, downloaded from http://www.fda.gov/downloads/advisorycommittees/commit-teesmeetingmaterials/pediatricadvisorycommittee/ucm351116.pdf on Mar. 16, 2015.
Allen et al., Evidence Report/Technology Assessment, No. 195, Inhaled Nitric Oxide in Preterm Infants, Chapter 1, AHRQ Publication No. 11-E001, 2010, 1-12.
Askie et al., "Inhaled nitric oxide in preterm infants: an individual-patient data meta-analysis of randomized trials," Pediatrics, 128(4):729-739 (2011).
Franconi et al., "Pharmacogenomics, pharmacokinetics and pharmacodynamics: interaction with biological differences between men and women," British Journal of Pharmacology, 171:580-594 (2014).
Tecklin, J., Environmental Aspects of Intensive Care: Equipment and Technologic Supports, Pediatric Physical Therapy, Fourth Edition, 2008, 120-123.
Yasuda et al., "The role of ethnicity in variability in response to drugs: focus on clinical pharmacology studies," Clinical Pharmacology & Therapeutics, 84(3):417-423 (2008).
The Study Group of the Eunice Kennedy Shriver NICHD Neonatal Research Network, The New England Journal of Medicine, 2010, 362(21), 1970-1979.
Mayo Clinic Staff, Pulmonary Hypertension, Symptoms, Mayo Clinic, 1998, 1-3.
Sandham, J., Extracorporeal Membrane Oxygenation (ECMO), EBME, 2012, 1-3.
Cleveland Clinic, Disease & Conditions, Pulmonary Hypertension: Causes, Symptoms, Diagnosis, Treatment; Cleveland Clinic, 1995, 1-4.
Benisty, J., Cardiology Patient Page, Pulmonary Hypertension, Circulation, 2002, 106, 1-4.
Rodriguez, R., "Management of Respiratory Distress Syndrome: An Update", *Respiratory Care*, Mar. 2003, vol. 48, No. 3, pp. 279-287.
Canadian Office Action for Canadian Application No. 2,855,261 dated Feb. 20, 2017 (13 pages).
Response to Canadian Office Action for Canadian Application No. 2,855,261 filed on Aug. 18, 2017 (56 pages).
Gadhia et al., "Effects of Early Inhaled Nitric Oxide Therapy and Vitamin A Supplementation on the Risk for Bronchopulmonary Dysplasia in Premature Newborns with Respiratory Failure," The Journal of Pediatrics, 164(4):744-748 (2014).
INO Therapeutics, Prescribing information for INOMAX-nitric oxide gas, 3 pages (2013).
Kinsella et al., "Inhaled nitric oxide in premature neonates with severe hypoxaemic respiratory failure: a randomized controlled trial," Lancet, 354:1061-1065 (1999).
Laughon et al., "Prediction of Bronchopulmonary Dysplasia by Postnatal Age in Extremely Premature Infants," Am. J. Respir. Crit. Care Med., 183:1715-1722 (2011).
Northway et al., "Pulmonary Disease Following Respirator Therapy of Hyaline-Membrane Disease," The New England Journal of Medicine, 276(7):357-368 (1967).
Konduri et al., "A Randomized Trial of Early Versus Standard Inhaled Nitric Oxide Therapy in Term and Near-Term Newborn Infants with Hypoxic Respiratory Failure," Pediatrics, 113(3):559-564 (2004).
Schreiber et al., "Inhaled Nitric Oxide in Premature Infants with the Respiratory Distress Syndrome," The New England Journal of Medicine, 349:2099-2107 (2003).
Mercier et al., "Inhaled nitric oxide for prevention of bronchopulmonary dysplasia in premature babies (EUNO): a randomised controlled trial," Lancet, 376:346-354 (2010).
Kinsella et al., "Early Inhaled Nitric Oxide Therapy in Premature Newborns with Respiratory Failure," The New England Journal of Medicine, 355:354-364 (2006).
Ballard et al., "Inhaled Nitric Oxide in Preterm Infants Undergoing Mechanical Ventilation," The New England Journal of Medicine, 355(4):343-353 (2006).
Ballard, "Inhaled Nitric Oxide in Preterm Infants—Correction," The New England Journal of Medicine, 357:1444-1445 (2007).
'ClinicalTrials.gov' [online]. "High-Frequency Oscillatory Ventilation Associated With Inhaled Nitric Oxide in Children," Jun. 2009, [retrieved on Nov. 3, 2015]. Retrieved from the Internet: URL≤https://clinicaltrials.gov/ct2/show/NCT00924846>, 3 pages.

(56) References Cited

OTHER PUBLICATIONS

"Giving Medication to Children: Q & A with Dianne Murphy, M.D.," FDA Consumer Health Information, U.S. Food and Drug Administration, Jun. 2009, 1-3.

Shah et al., "Nitric Oxide Treatment for Pulmonary Hypertension After Neonatal Cardiac Operation," Ann. Thorac. Surg., 1995, 1791-1793.

AARC Clinical Practice Guideline, "Neonatal Time-Triggered, Pressure-Limited, Time-Cycled Mechanical Ventilation," Respiratory Care, Aug. 1994, 39(8): 808-816.

AARC, Mechanical Ventilation: Ventilatory Techniques, Pharmacology, and Patient Management Strategies Part II, Respiratory Care, May 1996, 41(5): 134 pages.

Abman et al., "Inhaled Nitric Oxide Therapy of Pulmonary Hypertension and Respiratory Failure in Premature and Term Neonates," Advances in Pharmacology, 1995, 34: 457-474.

Adatia et al., "Inhaled nitric oxide and hemodynamic evaluation of patients with pulmonary hypertension before transplantation," J. Am. Coll. Cardiol., 1995, 25: 1656-64.

Adhikari et al., "Effect of nitric oxide on oxygenation and mortality in acute lung injury: systematic review and meta-analysis," BMJ, Mar. 23, 2007, pp. 1-8.

Aikio, "Pulmonary Nitric Oxide in Preterm and Term Infants With Respiratory Failure," Oulun Yliopisto, Oct. 2002, 74 pages.

Air Liquide Medicinal, VasoKINOX, retrieved from the Internet: URL<http://www.airliquidemedicin al.es/file/otherelement/pj/vasokinox46604.pdf>, May 2008, 9 pages.

Akmal et al., "Role of nitric oxide in management of acute respiratory distress syndrome," Annals of Thoracic Medicine, Jul.-Sep. 2008, 3(3): 100-103.

Allen et al., "Inhaled Nitric Oxide in Preterm Infants," Evidence Report/Technology Assessment, No. 195. (Prepared by Johns Hopkins University Evidence-based Practice Center under Contract No. 290-2007-10061-1). AHRQ Publication No. 11-E001. Rockville, MD: Agency for Healthcare Research and Quality, Oct. 2010, 315 pages.

Aloy[a] et al., "Recomendaciones para la utilización del óxido nítrico inhalado en patología neonatal," An. Pediatr. Barc, 2006, 64(3): 260-6.

Amended INOT22 Protocol, Excerpt from prosecution history of U.S. Pat. No. 8,795,741 (submitted as Appendix 3 to Dr. Baldassarre Declaration under 37 C.F.R. § 1.131), pp. 1-60.

AARC, Proceedings from a special symposium on Use of Inhaled Nitric Oxide in the Hypoxic Newborn, Presented at the 51st International Respiratory Congress of the American Association for Respiratory Care in San Antonio, Texas on Dec. 2005, 41 pages.

Angeja et al., "Evaluation and Management of Diastolic Heart Failure," Circulation, 2003, 107: 659-663.

Arcasoy et al., "Echocardiographic Assessment of Pulmonary Hypertension in Patients with Advanced Lung Disease," Am. J. Respir. Crit. Care Med., 2003, 167: 735-740.

Archer et al., "An evidence-based approach to the management of pulmonary arterial hypertension," Curr. Opin. Cardiol., 2006, 21:385-392.

Argenziano et al., "Randomized, Double-Blind Trial of Inhaled Nitric Oxide in LVAD Recipients With Pulmonary Hypertension," Ann. Thorac. Surg., 1998, 65: 340-5.

Arul et al., "Inhaled Nitric Oxide for Preterm Neonates," Clin. Perinatol., 2009, 36: 43-61.

Atz et al., "Diagnostic and Therapeutic Uses of Inhaled Nitric Oxide in Neonatal Ebstein's Anomaly," The American Journal of Cardiology, Apr. 1, 2003, 91: 906-908.

Australia INOmax Label/Product Information, Nov. 2007, 4 pages.

Balaguru et al., "Management of Heart Failure in Children," Curr. Probl. Pediatr., Jan. 2000, 30: 5-30.

Ballard et al., "Surfactant Function and Composition in Premature Infants Treated With Inhaled Nitric Oxide," Pediatrics, Aug. 2007, 120(2): 346-353.

Balzer et, al., "Inhaled Nitric Oxide as a Preoperative Test (INOP Test I) The INOP Test Study Group," Circulation, Sep. 2002, 106(suppl I): I-76-I-81.

Banjar, "Diagnosis and Management of Pulmonary Arterial Hypertension in the Pediatric Population (PH)," Bahrain Medical Bulletin, Dec. 2008, 30(4): 1-19.

Baysal, "Nitric Oxide II: Therapeutic Uses and Clinical Applications," Turk. J. Med. Sci., 2002, 32: 1-6.

Beasley et al., "Withdrawal of Fenoterol and the End of the New Zealand Asthma Mortality Epidemic," Int. Arch. Allergy Immunol., 1995, 107: 325-327.

Beghetti, "Inhaled Nitric Oxide Can Cause Severe Systemic Hypotension," J. Pediatr., 1997, 130: 844.

Beloucif et al., "A European survey of the use of inhaled nitric oxide in the ICU," Intensive Care Med, 1998, 24: 864-877.

Berger et al., "Clinical features of paediatric pulmonary hypertension: a registry study," Lancet, Feb. 11, 2012, 379: 537-46.

Bernasconi et al., "Inhaled Nitric Oxide Applications in Paediatric Practice," Images in Paediatric Cardiology, 2002, 4-29.

Bernd Mayer, Editor, Nitric Oxide: Handbook of Experimental Pharmacology, 2000, Chapter 17, 412-414.

Berner et al., "Inhaled Nitric Oxide to Test the Vasodilator Capacity of the Pulmonary Vascular Bed in Children With Long-Standing Pulmonary Hypertension and Congenital Heart Disease," The American Journal of Cardiology, Mar. 1, 1996, 77: 532-535.

Blaise et al., "Nitric oxide, cell signaling and cell death," Toxicology 208, 2005, 177-192.

Bouhemad et al., "Echocardiographic Doppler Assessment of Pulmonary Capillary Wedge Pressure in Surgical Patients with Postoperative Circulatory Shock and Acute Lung Injury," Anesthesiology, 2003, 98: 1091-100.

Boyle, "Nitric Oxide Delivery Via Nasal Cannula," Retrieved from the Internet: URL<http://www.rtmagazine.com/2007/02/nitric-oxide-delivery-via-nasal-cannula/>, Feb. 7, 2007, 6 pages.

Branson, "Delivery of Inhaled Nitric Oxide," AARC Symposium, 2000, 21-39.

Brief on Appeal filed Oct. 4, 2011 in U.S. Appl. No. 12/820,866, 211 pages.

Burrows et al., "Pulmonary hypertension in children: perioperative management:," Can. Anaesth. Soc. J., 1986, 33(5): 606-28.

Bushman, "Essentials of Nitric Oxide for the Pediatric (Cardiac) Anesthesiologist," Seminars in Cardiothoracic and Vascular Anesthesia, Mar. 2001, 5(1): 79-90.

Butt, "Recent Advances in Paediatric Ventilation," Critical Care & Resuscitation, 1999, 1: 85-92.

Carcillo et al., "Clinical practice parameters for hemodynamic support of pediatric and neonatal patients in septic shock," Crit. Care Med., 2002, 30(6): 1365-1378.

Carlquist, "Neonatal Use of Inhaled Nitric Oxide," Department of Neonatology, Astrid Lindgren Children's Hospital, 2012, 42 pages.

Center for Drug Evaluation and Research, Application No. NDA 20845, INOMAX, Final Printed Labeling, Retrieved from the Internet: URL<http://www.accessdata.fda.gov/drugsatfda_docs/nda/99/20845_inomax_prntlbl.pdf>, Aug. 9, 2000, 8 pages.

Chemla et al., "Haemodynamic evaluation of pulmonary hypertension," Eur. Respir., 2002, 20: 1314-1331.

Clark et al., "Low-Dose Nitric Oxide Therapy for Persistent Pulmonary Hypertension of the Newborn," New England J. Med., 2000, 342: 469-474.

Cornfield et al., "Randomized, Controlled Trial of Low-dose Inhaled Nitric Oxide in the Treatment of Term and Near-term Infants with Respiratory Failure and Pulmonary Hypertension," Pediatrics, 1999, 104: 1089-1094.

Corning, "Nitric Oxide," RC Educational Consulting Services, Inc., 2003, 1-14.

Matthews et al., "The Right Ventricular Failure Risk Score: A Pre-Operative Tool for Assessing the Risk of Right Ventricular Failure in Left Ventricular Assist Device Candidates," J. Am. Coll. Cardiol., Jun. 3, 2008, 51(22): 2163-2172.

Creagh-Brown et al., "Bench-to-bedside review: Inhaled nitric oxide therapy in adults," Critical Care, May 2009, 13: 1-8.

(56) References Cited

OTHER PUBLICATIONS

Critical Care Medicine Department, Critical Care Therapy and Respiratory Care Section, "Nitric Oxide Therapy," Policy No. 2, May 2000, 13 pages.
Curriculum vitae of Dr. Edward Lawson, dated Feb. 4, 2016, 27 pages.
Curriculum Vitae of Dr. Maurice Beghetti, 1-47.
Curriculum Vitae of Geoffrey L. Rosenthal, M.D., Ph.D., Aug. 14, 2015, 1-19.
Daftari et al., "Initial Experience with Sildenafil, Bosentan, and Nitric Oxide for Pediatric Cardiomyopathy Patients with Elevated Pulmonary Vascular Resistance before and after Orthotopic Heart Transplantation," Journal of Transplantation, Jan. 2010, 2010: 1-6.
Katerndahl, "When Plagiarism Becomes Research," Family Practice, 1991, 8(4): 382-383.
Davidson et al., "Inhaled Nitric Oxide for the Early Treatment of Persistent Pulmonary Hypertension of the Term Newborn: A Randomized, Double-Masked, Placebo-Controlled, Dose-Response, Multicenter Study," Pediatrics, 1998, 101: 325-334.
Day, "Right ventricular size is acutely decreased by inhaled nitric oxide in newborns with pulmonary hypertension," American Journal of Perinatology, 1998, 15(7): 445-451 (Abstract Only).
De Oliveira et al., "Inhaled Nitric Oxide in the Management of Persistent Pulmonary Hypertension of the Newborn: A Meta-Analysis," Rev. Hosp. Clín. Fac. Med. S. Paulo, Jul.-Aug. 2000, 55(4):145-154.
USPTO Notice of Abandonment in U.S. Appl. No. 14/454,373, dated Dec. 1, 2015, 2 pages.
USPTO Notice of Abandonment in U.S. Appl. No. 14/451,057, dated Dec. 16, 2015, 2 pages.
Declaration of James S. Baldassarre, M.D., Under 37 C.F.R. § 1.132, dated Dec. 4, 2013, submitted during prosecution of U.S. Pat. No. 8,846,112, 8 pages.
*Praxair Distrib., Inc. v. INO Therapeutics, Inc.*, Decision Denying Institution of Inter Partes Review Nos. IPR2015-00522, -00524, -00525, -00526, dated Jul. 29, 2015, 25 pages.
Declaration of Dr. Edward Lawson, dated Mar. 22, 2016, pp. 1-29.
Declaration of Dr. Maurice Beghetti in Support of Petition for Inter Partes Review of U.S. Pat. No. 8,846,112, dated Dec. 31, 2014, pp. 1-54.
Declaration of Dr. Maurice Beghetti in Support of Petition for Inter Partes Review of U.S. Pat. No. 8,431,163, dated Dec. 31, 2014, pp. 1-53.
Declaration of Dr. Maurice Beghetti in Support of Petition for Inter Partes Review of U.S. Pat. No. 8,282,966, dated Dec. 31, 2015, pp. 1-55.
Declaration of Geoffrey L. Rosenthal, M.D., Ph.D. in Support of Patent Owner's Preliminary Response to Praxair's Petition for Inter Partes Review of U.S. Pat. No. 8,282,966, dated Jun. 30, 2016, pp. 1-41.
Definition of "Contraindication" on Medicine.net.com, Retrieved from the Internet: URL<https://web.archive.org/web/20060812144659/http://www.medterms.com/script/main/art.asp?articlekey=17824>, Aug. 12, 2006, 2 pages.
Definition of Contraindication, MedlinePlus, Retrieved from the Internet: URL<https://web.archive.org/web/20090324033016/http://www.nlm.nih.gov/medlineplus/ency/article/002314.htm>, Mar. 24, 2009, 2 pages.
Desai et al., "Ventilatory Strategies and Adjunctive Therapy in ARDS," Indian J. Pediatr., Aug. 2006, 73(8): 661-668.
Drinkwater et al., "Modified Norwood operation for hypoplastic left heart syndrome," Ann. Thorac. Surg., 2001, 72: 2081-2087.
Durmowicz, "Pulmonary Edema in 6 Children With Down Syndrome During Travel to Moderate Altitudes," Pediatrics, Aug. 2001, 108: 443-447.
El-Khuffash, "Are B-type natriuretic peptide (BNP) and N-terminal-pro-BNP useful in neonates?" Arch. Dis. Child Fetal Neonatal Ed., 2007, 92: F320-F324.

Elshamaa et al., "Plasma Nitric Oxide Level in Myocardial Disorders with Left Ventricular Diastolic Dysfunction," J. Med. Sci., May-Jun. 2006, 6(3): 439-444.
Khilnani, "Inhaled Nitric Oxide (INO)," Practical Approach to Pediatric Intensive Care, 2005, 9 pages.
Farrow et al., "The Diseases Treated with ECMO: Focus on PPHN," Semin. Perinatal., 2005, 29: 8-14.
FDA, "What is a Serious Adverse Event?" Retrieved from the Internet: URL<http://web.archive.org/web/2009061102209/http://www.fd a.gov.Safety/MedWatch/HowToReport/ucm053087.htm>, Jun. 11, 2009, 2 pages.
Fernandez-Perez et al., "Inhaled Nitric Oxide for Acute Right-Ventricular Dysfunction After Extrapleural Pneumonectomy," Respir. Care, 2006, 51(10): 1172-1176.
Finer et al., "Nitric oxide for respiratory failure in infants born at or near term," The Cochrane Library, 2006, 4: 46 pages.
Fioretto et al., "Acute and sustained effects of early administration of inhaled nitric oxide to children with acute respiratory distress syndrome," Pediatr. Crit. Care Med., 2004, 5(5): 469-474.
Fojón et al., "Inhaled Nitric Oxide Through a Noninvasive Ventilation Device to Assess Reversibility of Pulmonary Hypertension in Selecting Recipients for Heart Transplant," Transplantation Proceedings, 2005, 37: 4028-4030.
Friesen et al., "Review article: Anesthetic management of children with pulmonary arterial hypertension," Pediatric Anesthesia, 2008 18: 208-216.
Frostell et al., "Inhaled Nitric Oxide: A Selective Pulmonary Vasodilator Reversing Hypoxic Pulmonary Vasoconstriction," Circulation, 1991, 83: 2038-2047.
Germann et al., "Inhaled Nitric Oxide Therapy in Adults: European Expert Recommendations," Intensive Care Med, 2005, 31: 1029-1041.
Ghofrani et al., "Pulmonary Vascular Diseases: Uncertainties in the Diagnosis and Treatment of Pulmonary Arterial Hypertension," Circulation, 2008, 118: 1195-1201.
Giaid et al., "Reduced Expression of Endothelial Nitric Oxide Synthase in the Lungs of Patients With Pulmonary Hypertension," N. Engl. J. Med., Jul. 27, 1995, 333: 214-21.
Gibbs, "Recommendations on the management of pulmonary hypertension in clinical practice," Heart, 2001, 86(Suppl I): il-il3.
Gidding, "The Importance of Randomized Controlled Trials in Pediatric Cardiology," JAMA, 2007, 298: 1214-1216.
Goldstein et al., "Inhaled Nitric Oxide is not a Negative Inotropic Agent in a Porcine Model of Pulmonary Hypertension," Thorac. Cardiovasc. Surg., 1997, 114: 461-6.
Gonzalez et al., "Randomized Controlled Trial of Early Compared with Delayed Use of Inhaled Nitric Oxide in Newborns with a Moderate Respiratory Failure and Pulmonary Hypertension," Journal of Perinatology, 2009, 333(4): 1-5.
Google Book Search: "neonatal respiratory" "nitric oxide" ("Google Book Search 2"), Search Performed on Jun. 1, 2016, 2 pages.
Google Book Search: "neonatal ventilation" "nitric oxide" ("Google Book Search 3"), Search Performed on Jun. 1, 2016, 2 pages.
Google Book Search: "neonatal" "nitric oxide" ("Google Book Search 1"), Search Performed on Jun. 1, 2016, 2 pages.
Gothberg et al., "Residual pulmonary hypertension in children after treatment with inhaled nitric oxide: a follow-up study regarding cardiopulmonary and neurological symptoms," Acta. Paediatr., 2000, 89: 1414-9.
Goyal et al., "Efficacy of nitroglycerin inhalation in reducing pulmonary arterial hypertension in children with congenital heart disease," British Journal of Anaesthesia, May 2006, 97(2): 208-14.
Griffiths et al. "Inhaled Nitric Oxide Therapy in Adults." New England Journal of Medicine, 2005, 353: 2683-2695.
Gurgueira, "Inhaled nitric oxide: clinical application considerations," J. Pneumologia, Sep.-Oct. 2003, 29(5): 7 pages.
Guyatt et al., "Users' Guide to the Medical Literature: A Manual for Evidenced-Based Clinical Practice," 2d ed., 2008, Chapter 2, pp. 9-16.
Harvard University Countway Library of Medicine, [HMS] EBM-Evidence-based Medicine, retrieved from the Internet: URL< http://guides.library.harvard.edu/hms/ebm>, Nov. 15, 2015, 1-3.

(56) References Cited

OTHER PUBLICATIONS

Hayward et al., "Review: Inhaled nitric oxide in cardiology practice," Cardiovascular Research, 1999, 43: 628-638.
Hayward et al., "Inhaled Nitric Oxide in Cardiac Failure: Vascular Versus Ventricular Effects," J. Cardiovascular Pharmacology, 1996, 27: 80-85.
Heinonen, "Synchronized Delivery of Inspired Nitric Oxide," Comprehensive Summaries of Uppsala Dissertations from the Faculty of Medicine, 2002, 1162: 1-58.
Henrichsen et al., "Inhaled nitric oxide can cause severe systemic hypotension," J. Pediatrics, 1996, 129(1): 183.
Hess, "Adverse Effects and Toxicity of Inhaled Nitric Oxide," Respir. Care, 1999, 44(3): 315-329.
Hess, "Use of Inhaled Nitric Oxide in Patients with Acute Respiratory Distress Syndrome," Respiratory Care, May 1996, 41(5): 424-46.
Hoehn, "Therapy of pulmonary hypertension in neonates and infants," Pharmacology & Therapeutics, 2007, 114: 318-326.
Hoeper et al., "A Comparison of the Acute Hemodynamic Effects of Inhaled Nitric Oxide and Aerosolized Iloprost in Primary Pulmonary Hypertension," Journal of the American College of Cardiology, Jan. 2000, 35(1): 176-182.
Hoeper et al., "Definitions and Diagnosis of Pulmonary Hypertension," J. of the American College of Cardiology, 2013, 62(25): D42-D50.
Hsu et al., "Heart Failure in Children Part I: History, Etiology, and Pathophysiology," Circ. Heart Fail., 2009, 2: 63-70.
Huang et al., "Left Ventricular Dysfunction in Children with Fulminant Enterovirus 71 Infection," Brief Report, Apr. 2002, 34: 1020-4.
Hunt et al., "ACC/AHA 2005 Guideline Update for the Diagnosis and Management of Chronic Heart Failure in the Adult," ACC/AHA Practice Guidelines, American College of Cardiology Foundation and the American Heart Association, 2005, e1-e82.
Ichinose et al., "Inhaled Nitric Oxide: A Selective Pulmonary Vasodilator: Current Uses and Therapeutic Potential," Circulation, 2004, 109: 3106-3111.
Ignarro, "Nitric Oxide Biology and Pathobiology," Academic Press, 2000, 1-13.
*INO Therapeutics LLC and Ikaria, Inc. v. Praxair Distribution, Inc. and Praxair, Inc.*, "Defendant's Initial Invalidity Contentions," C.A. No. 15-170-GMS, dated Dec. 15, 2015, 33 pages.
*INO Therapeutics LLC and Ikaria, Inc. v. Praxair Distribution, Inc. and Praxair, Inc.*, "Defendant's Initial Invalidity Contentions," C.A. No. 15-170-GMS, dated Dec. 15, 2015, Appendix A, 76 pages.
*INO Therapeutics LLC and Ikaria, Inc. v. Praxair Distribution, Inc. and Praxair, Inc.*, "Defendant's Initial Invalidity Contentions," C.A. No. 15-170-GMS, dated Dec. 15, 2015, Appendix B, 1624 pages.
INOmax Annex I—Summary of Product Characteristics; Annex II—Manufacturer(s) Responsible for Batch Release, Conditions or Restrictions Regarding Supply and Use, Other Conditions and Requirements of the Marketing Authorisation, Conditions or Restrictions with Regard to the Safe and Effective Use of the Medicinal Product; Annex III—Labeling and Package Leaflet, Nov. 23, 2009, 1-53.
*Praxair Distribution, Inc. v. Mallinckrodt Hospital Products IP LTD.*, decision on appeals from USPTO PTAB No. IPR2015-00529; 2016-2616, 2016-2656 (Fed. Cir. May 16, 2018), pp. 1-21, and opinion concurring in the judgement, pp. 1-9.
INOmax® Label, Full Prescribing Information, Oct. 2015, 11 pages.
Ivy et al., "Pediatric Pulmonary Hypertension," Journal of the American College of Cardiology, 2013, 62(25): Suppl D, 117-126.
Khilnani, Pediatric & Neonatal Mechanical Ventilation, 1st Ed., 2006, 197 pages.
Jonsen et al., "Clinical Ethics: A Practical Approach to Ethical Decisions in Clinical Medicine," 4th ed., McGraw-Hill Health Professions Division, 1998, 14 pages.
Kaldjian et al., "A Clinician's Approach to Clinical Ethical Reasoning," JGIM, 2005, 20: 306-311.
Kannan et al., "Nitric Oxide: Biological Role and Clinical Uses," Indian J. Pediatr., 1998, 65: 333-345.
Kaulitz et al., "Archives of Disease in Childhood: Current treatment and prognosis in children with functionally univentricular hearts," Arch. Dis. Child., 2005, 90: 757-762.
Keane et al., NADAS' Pediatric Cardiology, 2nd Edition, 2006, Chapter 10, 10 pages.
Kieler-Jensen et al., "Inhaled Nitric Oxide in the Evaluation of Heart Transplant Candidates with Elevated Pulmonary Vascular Resistance," Heart & Lung Transplant, 1994, 13: 366-375.
Kinsella et al., "Early Inhaled Nitric Oxide Therapy in Premature Newborns with Respiratory Failure," N. Engl. J. Med., 2006, 355: 354-64.
Kinsella et al., "Effects of Inhaled Nitric Oxide on Pulmonary Edema and Lung Neutrophil Accumulation in Severe Experimental Hyaline Membrane Disease," Pediatric Research, 1997, 41: 457-463.
Kinsella et al., "Inhaled nitric oxide in premature neonates with severe hypoxaemic respiratory failure: a randomised controlled trial," The Lancet, 1999, 354: 1061-1065.
Kinsella et al., "Inhaled nitric oxide therapy in children," Paediatric Respiratory Reviews, 2005, 6: 190-198.
Klabunde, "Pulmonary Capillary Wedge Pressure," Cardiovascular Physiology Concepts, Retrieved from the Internet: <http://www.cvphysiology.com/Heart%20Failure/HF008.htm>, Apr. 11, 2007, 2 pages.
Konduri, "Early inhaled nitric oxide therapy for term and near-term newborn infants with hypoxic respiratory failure: neurodevelopmental follow-up," J. Pediatr., 2007, 150(3): 235-240, 240.e.1.
Laitinen et al., "Postoperative Nitric Oxide Therapy in Children with Congenital Heart Disease," Scand. Cardiovasc. J., 2000, 34: 149-153.
Lipshultz, "Ventricular dysfunction clinical research in infants, children and adolescents," Progress in Pediatric Cardiology, 2000, 12: 1-28.
Loh et al., "Cardiovascular Effects of Inhaled Nitric Oxide in Patients with Left Ventricular Dysfunction," Circulation, 1994, 90: 2780-2785.
Lunn, "Subspecialty Clinics: Anesthesiology: Inhaled Nitric Oxide Therapy," Mayo Clin. Proc., 1995, 70: 247-255.
Macrae et al., "Inhaled Nitric Oxide Therapy in Neonates and Children: Reaching a European Consensus," Intensive Care Medicine, 2004, 30: 372-380.
*Mallinckrodt Hospital Products IP Ltd., INO Therapeutics LLC and Ikaria, Inc., v. Praxair Distribution, Inc., and Praxair, Inc.*, "Plaintiffs' Second Supplemental Objections and Responses to Praxair's Second Set of Interrogatories (No. 13).," C.A. No. 15-170 (GMS), dated Sep. 12, 2016, 31 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Expert Report of Alan H. Friedman, M.D.," dated Oct. 27, 2016, 82 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS.: Deposition Transcript dated Jan. 5, 2017 Deposition of Geoffrey Lahn Rosenthal, M.D., 99 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Proposed Joint Pretrial Order," dated Feb. 17, 2017, 13 pages (Redacted Version).
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Exhibit 1: Joint Statement of Uncontested Facts, dated Feb. 17, 2017, 12 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Exhibit 2.1: Plaintiffs' Statement of Contested Issues of Fact and Law, dated Feb. 17, 2017, 6 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Exhibit 2.2: Defendants' Statement of Contested Issues of Fact and Law, dated Feb. 17, 2017, 6 pages.

(56) References Cited

OTHER PUBLICATIONS

*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Defendants' Proposed Findings of Fact and Conclusions of Law," dated May 3, 2017, 58 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Plaintiffs' Proposed Findings of Fact and Conclusions of Law," dated May 3, 2017, 54 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Memorandum," dated Sep. 5, 2017, 45 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Order," dated Sep. 5, 2017, 1 page.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Judgment," dated Sep. 5, 2017, 2 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 1 of Bench Trial, dated Mar. 13, 2017, 102 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 2 of Bench Trial, dated Mar. 15, 2017, 103 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 3 of Bench Trial, dated Mar. 16, 2017, 97 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 4 of Bench Trial, dated Mar. 17, 2017, 107 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 5 of Bench Trial, dated Mar. 20, 2017, 93 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 6 of Bench Trial, dated Mar. 21, 2017, 87 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 7 of Bench Trial, dated Mar. 22, 2017, 36 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, PACER Docket, retrieved on Oct. 27, 2017, 47 pages.
Manktelow et al., "Physiologic Determinants of the Response to Inhaled Nitric Oxide in Patients with Acute Respiratory Distress Syndrome," Anesthesiology, 1997, 87: 297-307.
USPTO Notice of Abandonment in U.S. Appl. No. 14/482,704, dated Mar. 14, 2016, 2 pages.
Medical Card System, Inc., "Inhaled Nitric Oxide (INO) in Neonates," Medical Policy: MP-ME-01-08, Aug. 25, 2008, 1-12.
El-Segaier et al., "Nitric oxide in neonatal transposition of the great arteries," Acta Paediatrica, 2005, 94: 912-916.
Morris et al., "Inhaled nitric oxide as a selective pulmonary vasodilator in clinical anesthesia," Journal of the American Association of Nurse Anesthetists, Feb. 1997, 65(1): 59-67.
Mourani et al., "Effects of Long-term Sildenafil Treatment for Pulmonary Hypertension in Infants with Chronic Lung Disease," J. Pediatr., Mar. 2009, 154(3): 379-384.
Myers, "Therapeutic Gases for Neonatal and Pediatric Respiratory Care," Respiratory Care, Apr. 2003, 48(4): 399-425.
Nakagawa et al., "Dose response to inhaled nitric oxide in pediatric patients with pulmonary hypertension and acute respiratory distress syndrome," The Journal of Pediatrics, Jul. 1997, 131: 63-69.
Namachivayam et al., "Sildenafil Prevents Rebound Pulmonary Hypertension after Withdrawal of Nitric Oxide in Children," Am. J. Respir. Crit. Care Med., 2006, 174: 1042-1047.
Greenough, Neonatal Respiratory Disorders, 2d ed., 2003, 568 pages.
National Pulmonary Hypertension Centres of the UK and Ireland, Consensus statement on the management of pulmonary hypertension in clinical practice in the UK and Ireland: Thorax, 2008, 63: (Suppl II): ii1-ii41.
Norman et al., "Criteria, Protocols and Reporting Forms for Initial Left Ventricular Assist Device Clinical Trials," Cardiovascular Diseases, Bulletin of the Texas Heart Institute, 1975, 2(3): 438-445.
Original INOT22 Protocol, Excerpt from prosecution history of U.S. Pat. No. 8,795,741 (submitted as Appendix 1 to Dr. Baldassarre Declaration under 37 C.F.R. § 1.131), pp. 1-58.
Oudiz et al., "Cardiac Catheterization in Pulmonary Arterial Hypertension: An Updated Guide to Proper Use," Retrieved from the Internet: URL≤http://www.phaonlineuniv.org/Journal/Article.cfm?ItemNumber=645>, 2005, 4(3): 1-10.
Patent Owner's Exhibit 2001 in IPR2015-00529: Supplemental Remarks filed May 9, 2012 in U.S. Appl. No. 12/821,020, 22 pages.
Patent Owner's Exhibit 2002 in IPR2015-00529: Non-Final Office Action dated Jan. 31, 2012, in U.S. Appl. No. 12/821,020, 23 pages.
Patent Owner's Exhibit 2014 in IPR2015-00529: Interview Summary dated Sep. 9, 2010 in U.S. Appl. No. 12/821,020 ('966 Patent), 4 pages.
Patent Owner's Exhibit 2019 in IPR2015-00529: Patent Owner's Updated Power of Attorney, dated Oct. 29, 2015, 3 pages.
Patent Owner's Exhibit 2020 in IPR2015-00529: Declaration of Geoffrey L. Rosenthal, M.D., Ph.D. in Support of Patent Owner's Response to Praxair's Petition for Inter Partes Review of U.S. Pat. No. 8,846,112, dated Nov. 5, 2015, 56 pages.
Patent Owner's Exhibit 2022 in IPR2015-00529: Deposition of Dr. Maurice Beghetti, dated Oct. 12, 2015, 283 pages.
Patent Owner's Exhibit 2035 in IPR2015-00529: Nitroglycerin in 5% Dextrose Injection Label, Oct. 2014, pp. 1-12.
Patent Owner's Exhibit 2036 in IPR2015-00529: Hearing Before the Board During the Deposition of Geoffrey L. Rosenthal, M.D., Ph.D., dated Jan. 5, 2016, pp. 1-14.
*Praxair Distrib., Inc. v. INO Therapeutics, Inc.*, Petition for Inter Partes Review of U.S. Pat. No. 8,431,163, filed Jan. 5, 2015, 59 pages.
Juliana et al., "Severe Persistent Pulmonary Hypertension of the Newborn in a Setting Where Limited Resources Exclude the use of Inhaled Nitric Oxide: Successful Treatment with Sildenafil," Eur. J. Pediatr., 2005, 164: 626-629.
Petitioner's Exhibit 1033 in IPR2015-00522: Claim Chart for Claims 1-3, 5-9, 11, 13-17, 20, 22-25, and 28, pp. 1-35.
Petitioner's Exhibit 1034 in IPR2015-00522: Claim Chart for Claims 4, 10, 12, 18, 19, 21, 26, 27, and 29, pp. 1-4.
Petitioner's Exhibit 1035 in IPR2015-00522: Claim Chart for Claims 1-29, pp. 1-44.
Petitioner's Exhibit 1036 in IPR2015-00524: Claim Chart for Claims 1-3, 5-9, 11, 13-14, 16-18, 21, 23-27, and 29, pp. 1-36.
Petitioner's Exhibit 1037 in IPR2015-00524: Claim Chart for Claims 4, 10, 12, 15, 19, 20, 22, 28, and 30, pp. 1-4.
Petitioner's Exhibit 1038 in IPR2015-00524: Claim Chart for Claims 1-30, pp. 1-41.
Petitioner's Exhibit 1039 in IPR2015-00525: Claim Chart for Claims 1, 2, 4, 6, 7, 9, 11-13, 15, 18, 20, 21, 23, and 25, pp. 1-26.
Petitioner's Exhibit 1040 in IPR2015-00525: Claim Chart for Claims 3, 5, 8, 10, 14, 16, 17, 19, 22, and 24, pp. 1-4.
Petitioner's Exhibit 1041 in IPR2015-00525: Claim Chart for Claims 1-25, pp. 1-34.
Petitioner's Exhibit 1042 in IPR2015-00526: Claim Chart for Claims 1, 2, 4, 6-14, 17-23, 31-32, 34-35, 37-40, and 42-44, pp. 1-69.
Petitioner's Exhibit 1043 in IPR2015-00526: Claim Chart for Claims 3, 5, 15, 16, 36 and 41, pp. 1-3.

(56) References Cited

OTHER PUBLICATIONS

Petitioner's Exhibit 1044 in IPR2015-00526: Claim Chart for Claims 1-23, 31-32, and 34-44, pp. 1-100.
Petitioner's Exhibit 1045 in IPR2015-00526: Claim Chart for Claims 24-27, 29-30 and 33, pp. 1-17.
Petitioner's Exhibit 1046 in IPR2015-00526: Claim Chart for Claim 28, 1 page.
Petitioner's Exhibit 1047 in IPR2015-00526: Claim Chart for Claims 24-30 and 33, pp. 1-19.
Petitioner's Exhibit 1048 in IPR2015-00529: Claim Chart.
Petitioner's Exhibit 1051 in IPR2015-00526: Webster's Third New International Dictionary of the English Language Unabridged, 2002, 385-388.
Petitioner's Exhibit 1058 in IPR2015-00529: E-mails between B. Steinberg and B. Weed RE: Praxair/Ikaria—IPR2015-00529—PO Witness Deposition Scheduling, dated Dec. 14, 2015, Dec. 17, 2015, Dec. 18, 2015, and Dec. 30, 2015, 3 pages.
Pilbeam, Mechanical Ventilation, Special Techniques in Mechanical Ventilation, § 4: Nitric Oxide, 4th ed., 2006, 1-16.
Plaintiff's Opposition to Defendants' Motion for Judgment on the Pleadings for Counts I-V of Plaintiffs' Complaint, Case No. 2015-cv-00170, Docket No. 54, dated Jan. 27, 2016, 540 pages.
Pozzoli et al., "Non-invasive Estimation of Left Ventricular Filling Pressures by Doppler Echocardiography," Eur. J. Echocardiography, 2002, 3: 75-79.
*Praxair Distribution, Inc. and NOxBOX Limited v. Mallinckrodt Hospital Products IP Ltd., and INO Therapeutics, Inc. d/b/a Ikaria, Inc.*, IPR2016-00777, "Petition for Inter Partes Review of U.S. Pat. No. 8,282,966," dated Mar. 23, 2016, 59 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00777, "Notice of Filing Date Accorded to Petition and Time for Filing Patent Owner Preliminary Response," dated Mar. 30, 2016, 5 pages.
*Praxair Distribution, Inc. and NOxBOX Limited v. Mallinckrodt Hospital Products IP Ltd.*, IPR2016-00777, "Patent Owner's Mandatory Notices," dated Apr. 13, 2016, 8 pages.
*Praxair Distribution, Inc. and NOxBOX Limited v. Mallinckrodt Hospital Products IP Ltd.*, IPR2016-00777, "Patent Owner's Preliminary Response," dated Jun. 30, 2016, 70 pages.
*Praxair Distribution, Inc. and NOxBOX Limited v. Mallinckrodt Hospital Products IP Ltd.*, IPR2016-00777, "Patent Owner's Exhibit List," dated Jun. 30, 2016, 6 pages.
*Praxair Distribution, Inc. and NOxBOX Limited v. Mallinckrodt Hospital Products IP Ltd.*, "Decision Denying Institution of Inter Partes Review for IPR2016-00777 (U.S. Pat. No. 8,282,966 B2); IPR2016-00778 (U.S. Pat. No. 8,431,163 B2); IPR2016-00779 (U.S. Pat. No. 8,293,284 B2); IPR2016-00780 (U.S. Pat. No. 8,795,741 B2)," dated Sep. 22, 2016, 13 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00778, "Praxair Distribution, Inc.'s Power of Attorney for Inter Partes Review of U.S. Pat. Nos. 8,282,966; 8,293,284; 8,431,163; 8,795,741; and 8,846,112," dated Mar. 22, 2016, 4 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00778, "NOxBOX Limited's Power of Attorney for Inter Partes Review of U.S. Pat. Nos. 8,28,966; 8,293,284; 8,431,163; 8,795,741; and 8,846,112," dated Mar. 18, 2016, 3 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00778, "NOxBOX Limited's Power of Attorney for Inter Partes Review of U.S. Pat. Nos. 8,28,966; 8,293,284; 8,431,163; 8,795,741; and 8,846,112," dated Mar. 23, 2016, 4 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00778, "Petition for Inter Partes Review of U.S. Pat. No. 8,431,163," dated Mar. 23, 2016, 59 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00778, "Notice of Filing Date Accorded to Petition and Time for Filing Patent Owner Preliminary Response," dated Mar. 30, 2016, 5 pages.
*Praxair Distribution, Inc. and NOxBOX Limited v. Mallinckrodt Hospital Products IP Ltd.*, IPR2016-00778, "Patent Owner's Mandatory Notices," dated Apr. 13, 2016, 8 pages.
*Praxair Distribution, Inc. and NOxBOX Limited v. Mallinckrodt Hospital Products IP Ltd.*, IPR2016-00778, "Patent Owner's Preliminary Response," dated Jun. 30, 2016, 70 pages.
*Praxair Distribution, Inc. and NOxBOX Limited v. Mallinckrodt Hospital Products IP Ltd.*, IPR2016-00778, "Patent Owner's Exhibit List," dated Jun. 30, 2016, 6 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00779, "Petition for Inter Partes Review of U.S. Pat. No. 8,293,284," dated Mar. 23, 2016, 60 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00779, "Notice of Filing Date Accorded to Petition and Time for Filing Patent Owner Preliminary Response," dated Mar. 30, 2016, 5 pages.
*Praxair Distribution, Inc. and NOxBOX Limited v. Mallinckrodt Hospital Products IP Ltd.*, IPR2016-00779, "Patent Owner's Mandatory Notices," dated Apr. 13, 2016, 8 pages.
*Praxair Distribution, Inc. and NOxBOX Limited v. Mallinckrodt Hospital Products IP Ltd.*, IPR2016-00779, "Patent Owner's Preliminary Response," dated Jun. 30, 2016, 69 pages.
*Praxair Distribution, Inc. and NOxBOX Limited v. Mallinckrodt Hospital Products IP Ltd.*, IPR2016-00779, "Patent Owner's Exhibit List," dated Jun. 30, 2016, 6 pages.
*Praxair Distribution, Inc. and NOxBOX Limited v. Mallinckrodt Hospital Products IP Ltd.*, IPR2016-00779, "BPAI Routing Sheet," dated Sep. 22, 2016, 1 page.
*Praxair Distribution, Inc. and NOxBOX Limited v. Mallinckrodt Hospital Products IP Ltd., and INO Therapeutics, Inc. d/b/a Ikaria, Inc.*, IPR2016-00780, "Petition for Inter Partes Review of U.S. Pat. No. 8,795,741," dated Mar. 23, 2016, 62 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00780, "Notice of Filing Date Accorded to Petition and Time for Filing Patent Owner Preliminary Response," dated Apr. 5, 2016, 5 pages.
*Praxair Distribution, Inc. and NOxBOX Limited v. Mallinckrodt Hospital Products IP Ltd.*, IPR2016-00780, "Patent Owner's Mandatory Notices," dated Apr. 13, 2016, 8 pages.
*Praxair Distribution, Inc. and NOxBOX Limited v. Mallinckrodt Hospital Products IP Ltd.*, IPR2016-00780, "Patent Owner's Preliminary Response," dated Jun. 30, 2016, 69 pages.
*Praxair Distribution, Inc. and NOxBOX Limited v. Mallinckrodt Hospital Products IP Ltd.*, IPR2016-00780, "Patent Owner's Exhibit List," dated Jun. 30, 2016, 6 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00781, "Petition for Inter Partes Review of U.S. Pat. No. 8,846,112," dated Mar. 23, 2016, 62 pages.
*Praxair Distribution, Inc. and NOxBOX Limited v. Mallinckrodt Hospital Products IP Ltd., and INO Therapeutics, Inc. d/b/a Ikaria, Inc.*, IPR2016-00781, "Notice of Filing Date Accorded to Petition and Time for Filing Patent Owner Preliminary Response," dated Apr. 5, 2016, 5 pages.
*Praxair Distribution, Inc. and NOxBOX Limited v. Mallinckrodt Hospital Products IP Ltd.*, IPR2016-00781, "Patent Owner's Mandatory Notices," dated Apr. 13, 2016, 8 pages.
*Praxair Distribution, Inc. and NOxBOX Limited v. Mallinckrodt Hospital Products IP Ltd.*, IPR2016-00781, "Patent Owner's Preliminary Response," dated Jun. 6, 2016, 71 pages.
*Praxair Distribution, Inc. and NOxBOX Limited v. Mallinckrodt Hospital Products IP Ltd.*, IPR2016-00781, "Patent Owner's Exhibit List," dated Jun. 6, 2016, 6 pages.

(56) References Cited

OTHER PUBLICATIONS

*Praxair Distribution, Inc. and NOxBOX Limited v. Mallinckrodt Hospital Products IP Ltd.*, IPR2015-00522, "Request for Refund of Post-Institution Fees," dated May 9, 2016, 4 pages.
*Praxair Distribution, Inc. and NOxBOX Limited v. Mallinckrodt Hospital Products IP Ltd.*, IPR2015-00522, "Notice of Refund," dated May 11, 2016, 2 pages.
*Praxair Distribution, Inc. and Praxair, Inc. v. INO Therapeutics LLC and Ikaria, Inc.*, IPR2015-00529, "Petitioner's Notice of Deposition of Geoffrey Rosenthal, M.D., Ph.D.," dated Dec. 26, 2015, 3 pages.
*Praxair Distribution, Inc. and Praxair, Inc. v. INO Therapeutics LLC and Ikaria, Inc.*, IPR2015-00529, "Petitioner's Reply to Patent Owner's Response to Petition," dated Jan. 15, 2015, 28 pages.
*Praxair Distribution, Inc. and Praxair, Inc. v. INO Therapeutics LLC and Ikaria, Inc.*, IPR2015-00529, "Petitioner's Updated Exhibit List," dated Jan. 15, 2015, 8 pages.
*Praxair Distribution, Inc. and Praxair, Inc. v. INO Therapeutics LLC and Ikaria, Inc.*, IPR2015-00525, "Notice of Filing Date Accorded to Petition and Time for Filing Patent Owner Preliminary Response," dated Feb. 6, 2015, 3 pages.
*Praxair Distribution, Inc. and Praxair, Inc. v. INO Therapeutics LLC and Ikaria, Inc.*, PR2015-00526, "Notice of Filing Date Accorded to Petition and Time for Filing Patent Owner Preliminary Response," dated Feb. 6, 2015, 3 pages.
*Praxair Distribution, Inc. and Praxair, Inc. v. INO Therapeutics LLC and Ikaria, Inc.*, IPR2015-00526, "Petitioner's Updated Mandatory Notices," dated Feb. 25, 2015, 4 pages.
*Praxair Distribution, Inc. and Praxair, Inc. v. Mallinckrodt Hospital Products IP Ltd.*, IPR2015-00525, "Request for Refund of Post-Institution Fees," dated May 9, 2016, 4 pages.
*Praxair Distribution, Inc. and Praxair, Inc. v. Mallinckrodt Hospital Products IP Ltd.*, IPR2015-00525, "Notice of Refund," dated May 11, 2016, 2 pages.
*Praxair Distribution, Inc. and Praxair, Inc. v. Mallinckrodt Hospital Products IP Ltd.*, IPR2015-00526, "Request for Refund of Post-Institution Fees," dated May 9, 2016, 4 pages.
*Praxair Distribution, Inc. and Praxair, Inc. v. Mallinckrodt Hospital Products IP Ltd.*, IPR2015-00526, "Notice of Refund," dated May 11, 2016, 2 pages.
*Praxair Distribution, Inc. and Praxair, Inc., v. INO Therapeutics LLC, and Ikaria, Inc.*, IPR 2015-00524, "Petitioner's Updated Mandatory Notices," dated Feb. 25, 2015, 4 pages.
*Praxair Distribution, Inc. and Praxair, Inc., v. INO Therapeutics LLC, and Ikaria, Inc.*, IPR 2015-00524, "Notice of Filing Date Accorded to Petition and Time for Filing Patent Owner Preliminary Response," dated Feb. 4, 2015, 3 pages.
*Praxair Distribution, Inc. and Praxair, Inc., v. INO Therapeutics LLC, and Ikaria, Inc.*, IPR2015-00529, "Notice of Filing Date Accorded to Petition and Time for Filing Patent Owner Preliminary Response," dated Feb. 6, 2015, 3 pages.
*Praxair Distribution, Inc. and Praxair, Inc., v. Mallinckrodt Hospital Products IP Ltd.*, IPR 2015-00524, "Request for Refund of Post-Institution Fees," dated May 9, 2016, 4 pages.
*Praxair Distribution, Inc. and Praxair, Inc., v. Mallinckrodt Hospital Products IP Ltd.*, IPR 2015-00524, "Notice of Refund," dated May 11, 2016, 2 pages.
*Praxair Distribution, Inc. v. INO Therapeutics LLC*, IPR2015-00525, "INO Therapeutics LLC Mandatory Notices," dated Jan. 26, 2015, 5 pages.
*Praxair Distribution, Inc. v. INO Therapeutics LLC*, IPR2015-00525, "Patent Owner's Amended Mandatory Notice," dated Feb. 25, 2015, 4 pages.
*Praxair Distribution, Inc. v. INO Therapeutics LLC*, IPR2015-00525, "Preliminary Response by Patent Owner," dated May 6, 2015, 74 pages.
*Praxair Distribution, Inc. v. INO Therapeutics LLC*, IPR2015-00525, "Patent Owner's Amended Mandatory Notice," dated May 7, 2015, 4 pages.
*Praxair Distribution, Inc. v. INO Therapeutics LLC*, IPR2015-00526, "INO Therapeutics LLC Mandatory Notices," dated Jan. 26, 2015, 5 pages.
*Praxair Distribution, Inc. v. INO Therapeutics LLC*, IPR2015-00526, "Patent Owner's Amended Mandatory Notice," dated Feb. 25, 2015, 4 pages.
*Praxair Distribution, Inc. v. INO Therapeutics LLC*, IPR2015-00526, "Preliminary Response by Patent Owner," dated May 6, 2015, 73 pages.
*Praxair Distribution, Inc. v. INO Therapeutics LLC*, IPR2015-00526, "Patent Owner's Exhibit List," dated May 6, 2016, 5 pages.
*Praxair Distribution, Inc. v. INO Therapeutics LLC*, IPR2015-00526, "Patent Owner's Amended Mandatory Notice," dated May 7, 2015, 4 pages.
*Praxair Distribution, Inc. v. INO Therapeutics LLC*, IPR2015-00529, "INO Therapeutics LLC Mandatory Notices," dated Jan. 26, 2015, 5 pages.
*Praxair Distribution, Inc. v. INO Therapeutics LLC*, IPR2015-00529, "Patent Owner's Amended Mandatory Notice," dated Feb. 25, 2015, 4 pages.
*Praxair Distribution, Inc. v. INO Therapeutics LLC*, IPR2015-00529, "Preliminary Response by Patent Owner," dated May 6, 2015, 66 pages.
*Praxair Distribution, Inc. v. INO Therapeutics LLC*, IPR2015-00529, "Patent Owner's Exhibit List," dated May 6, 2015, 6 pages.
*Praxair Distribution, Inc. v. INO Therapeutics LLC*, IPR2015-00529, "Patent Owner's Amended Mandatory Notice," dated May 7, 2015, 4 pages.
*Praxair Distribution, Inc. v. INO Therapeutics LLC*, IPR2015-00529, "Decision of Institution of Inter Partes Review," dated Jul. 29, 2015, 26 pages.
*Praxair Distribution, Inc. v. INO Therapeutics LLC*, IPR2015-00529, "Case Management and Scheduling Order," dated Jul. 30, 2015, 7 pages.
*Praxair Distribution, Inc. v. INO Therapeutics LLC*, IPR2015-00529, "Order Conduct of the Proceeding," dated Sep. 17, 2015, 5 pages.
*Praxair Distribution, Inc. v. INO Therapeutics LLC*, IPR2015-00529, "Patent Owner's Notice of Deposition of Dr. Maurice Beghetti," dated Sep. 28, 2015, 3 pages.
*Praxair Distribution, Inc. v. INO Therapeutics LLC*, IPR2015-00529, "Notice of Stipulation to Modify the Scheduling Order," dated Oct. 29, 2015, 4 pages.
*Praxair Distribution, Inc. v. INO Therapeutics LLC*, IPR2015-00529, "Decision: Patent Owner's Motion for Withdrawal and Substitution of Counsel," dated Oct. 30, 2015, 3 pages.
*Praxair Distribution, Inc. v. INO Therapeutics LLC*, IPR2015-00529, "Patent Owner's Updated Mandatory Notice," dated Nov. 3, 2015, 4 pages.
*Praxair Distribution, Inc. v. INO Therapeutics LLC*, IPR2015-00529, "Patent Owner INO Therapeutics LLC's Response to Praxair Distribution Inc's Petition for Inter Partes Review of U.S. Pat. No. 8,846,112," dated Nov. 5, 2015, 65 pages.
*Praxair Distribution, Inc. v. INO Therapeutics LLC*, IPR2015-00529, "Patent Owner's Updated Exhibit List," dated Nov. 5, 2015, 6 pages.
*Praxair Distribution, Inc. v. INO Therapeutics LLC*, IPR2015-00529, "Petitioner Praxair Distribution Inc.'s Objections to Patent Owner INO Therapeutics, LLC's Evidence," dated Nov. 13, 2015, 4 pages.
*Praxair Distribution, Inc. v. INO Therapeutics LLC*, IPR2015-00529, "Patent Owner's Updated Mandatory Notice," dated Dec. 4, 2015, 4 pages.
*Praxair Distribution, Inc. v. INO Therapeutics LLC*, IPR2015-00529, "Order Conduct of the Proceeding," dated Dec. 22, 2015, 4 pages.
*Praxair Distribution, Inc. v. INO Therapeutics LLC*, IPR2015-00529, "Patent Owner's Updated Mandatory Notices," dated Feb. 10, 2016, 5 pages.
*Praxair Distribution, Inc. v. INO Therapeutics LLC*, IPR2015-00529, "Order: Requests for Oral Argument," dated Feb. 24, 2016, 4 pages.

(56) References Cited

OTHER PUBLICATIONS

*Praxair Distribution, Inc. v. INO Therapeutics LLC*, IPR2015-00529, "Order: Requests for Oral Argument," dated Mar. 22, 2016, 4 pages.
*Praxair Distribution, Inc. v. INO Therapeutics LLC*, IPT2015-00525, "Patent Owner's Exhibit List," dated May 6, 2015, 6 pages.
*Praxair Distribution, Inc. v. INO Therapeutics, Inc. and Ikaria, Inc.*, IPR2015-00522, "Notice of Filing Date Accorded to Petition and Time for Filing Patent Owner Preliminary Response," dated Feb. 4, 2015, 3 pages.
*Praxair Distribution, Inc. v. INO Therapeutics, Inc. and Ikaria, Inc.*, IPR2015-00522, "Petitioner's Updated Mandatory Notices," dated Feb. 25, 2015, 4 pages.
*Praxair Distribution, Inc. v. INO Therapeutics, Inc. d/b/a Ikaria, Inc.*, IPR2015-00526, "Petition for Inter Partes Review of U.S. Pat. No. 8,795,741," dated Jan. 5, 2015, 72 pages.
*Praxair Distribution, Inc. v. INO Therapeutics, Inc. d/b/a Ikaria, Inc.*, IPR2015-0529, Petition for Inter Partes Review of U.S. Pat. No. 8,846,112, dated Jan. 5, 2015, 72 pages.
*Praxair Distribution, Inc. v. INO Therapeutics, Inc. d/b/a Ikaria, Inc.*, IPR2015-00522, "Petition for Inter Partes Review of U.S. Pat. No. 8,282,966," dated Jan. 5, 2015, 70 pages.
*Praxair Distribution, Inc. v. INO Therapeutics, Inc.*, "Decision: Denying Institution of Inter Partes Review for IPR2015-00522 (U.S. Pat. No. 8,282,966 B2); IPR2015-00524 (U.S. Pat. No. 8,293,284 B2); IPR2015-00525 (U.S. Pat. No. 8,431,163 B2); IPR2015-00526 (U.S. Pat. No. 8,795,741 B2)," dated Jul. 29, 2015, 25 pages.
*Praxair Distribution, Inc. v. INO Therapeutics, Inc.*, IPR2015-00522, "INO Therapeutics LLC Mandatory Notices in an Inter Partes Review of U.S. Pat. No. 8,282,966," dated Jan. 26, 2015, 5 pages.
*Praxair Distribution, Inc. v. INO Therapeutics, Inc.*, IPR2015-00522, "Patent Owner's Amended Mandatory Notice," dated Feb. 25, 2015, 4 pages.
*Praxair Distribution, Inc. v. INO Therapeutics, Inc.*, IPR2015-00522, "Preliminary Response by Patent Owners," dated May 4, 2015, 71 pages.
*Praxair Distribution, Inc. v. INO Therapeutics, Inc.*, IPR2015-00522, "Patent Owner's Exhibit List," dated May 4, 2015, 5 pages.
*Praxair Distribution, Inc. v. INO Therapeutics, Inc.*, IPR2015-00522, "Patent Owner's Amended Mandatory Notice," dated May 7, 2015, 4 pages.
*Praxair Distribution, Inc. v. Mallinckrodt Hospital Products IP Ltd.*, IPR2015-00529, Patent Owner's Sur-Reply to Praxair Distribution, Inc.'s Petition for Inter Partes Review of U.S. Pat. No. 8,846,112, dated Feb. 10, 2016, 13 pages.
*Praxair Distribution, Inc. v. Mallinckrodt Hospital Products IP Ltd.*, IPR2015-00529, "Patent Owner's Request for Oral Argument," dated Feb. 22, 2016, 3 pages.
*Praxair Distribution, Inc. v. Mallinckrodt Hospital Products IP Ltd.*, IPR2015-00529, "Petitioner's Request for Oral Argument," dated Feb. 22, 2016, 4 pages.
*Praxair Distribution, Inc. v. Mallinckrodt Hospital Products IP Ltd.*, IPR2015-00529, "Petitioner's Updated Mandatory Notices," dated Mar. 4, 2016, 4 pages.
*Praxair Distribution, Inc. v. Mallinckrodt Hospital Products IP Ltd.*, IPR2015-00529, "Patent Owner's Objections to Petitioner's Demonstratives," dated Mar. 24, 2016, 5 pages.
*Praxair Distribution, Inc. v. Mallinckrodt Hospital Products IP Ltd.*, IPR2015-00529, "Petitioner's Objections to Patent Owner's Demonstrative Exhibits," dated Mar. 24, 2016, 3 pages.
*Praxair Distribution, Inc. v. Mallinckrodt Hospital Products IP Ltd.*, IPR2015-00529, "Patent Owner's Transmittal Letter Accompanying Submission of Exhibit 2036," dated Mar. 30, 2016, 3 pages.
*Praxair Distribution, Inc. v. Mallinckrodt Hospital Products IP Ltd.*, IPR2015-00529, "Patent Owner's Updated Exhibit List," dated Mar. 30, 2016, 6 pages.
*Praxair Distribution, Inc. v. Mallinckrodt Hospital Products IP Ltd.*, IPR2015-00529, "Oral Argument Transcript, Oral Argument Held Mar. 29, 2016," 66 pages.
*Praxair Distribution, Inc. v. Mallinckrodt Hospital Products IP Ltd.*, IPR2015-00529, "Confirmation of Change of Patent Ownership Filed in Feb. 10, 2016 Updated Mandatory Notices," dated Jun. 20, 2016, 3 pages.
*Praxair Distribution, Inc. v. Mallinckrodt Hospital Products IP Ltd.*, IPR2015-00529, "Petitioner's Updated Mandatory Notices," dated Jul. 5, 2016, 3 pages.
*Praxair Distribution, Inc. v. Mallinckrodt Hospital Products IP Ltd.*, IPR2015-00529, "Final Written Decision," dated Jul. 7, 2016, 47 pages.
*Praxair Distribution, Inc. v. Mallinckrodt Hospital Products IP Ltd.*, IPR2015-00529, "Petitioner's Notice of Appeal," dated Sep. 6, 2016, 4 pages.
*Praxair Distribution, Inc. v. Mallinckrodt Hospital Products IP Ltd.*, IPR2015-00529, "Patent Owner's Notice of Cross-Appeal," dated Sep. 16, 2016, 52 pages.
*Praxair Distribution, Inc., and Praxair, Inc. v. INO Therapeutics, LLC and Ikaria, Inc.*, "Petitioner's Updated Mandatory Notices," dated Feb. 25, 2015, 4 pages.
*Praxair Distribution, Inc., v. INO Therapeutics LLC*, IPR 2015-00524, "INO Therapeutics LLC Mandatory Notices," dated Jan. 26, 2015, 5 pages.
*Praxair Distribution, Inc., v. INO Therapeutics LLC*, IPR 2015-00524, "Patent Owner's Amended Mandatory Notice," dated Feb. 25, 2015, 4 pages.
*Praxair Distribution, Inc., v. INO Therapeutics LLC*, IPR 2015-00524, "Preliminary Response by Patent Owners," dated May 4, 2015, 69 pages.
*Praxair Distribution, Inc., v. INO Therapeutics LLC*, IPR 2015-00524, "Patent Owner's Exhibit List," dated May 4, 2015, 5 pages.
*Praxair Distribution, Inc., v. INO Therapeutics LLC*, IPR 2015-00524, "Patent Owner's Amended Mandatory Notice," dated May 7, 2015, 4 pages.
*Praxair Distribution, Inc., v. INO Therapeutics, Inc. d/b/a Ikaria, Inc.*, IPR 2015-00524, "Petition for Inter Partes Review of U.S. Pat. No. 8,293,284," dated Jan. 5, 2015, 68 pages.
*Praxair Distribution, Inc., v. INO Therapeutics, Inc. d/b/a Ikaria, Inc.*, IPR2015-00525, "Petition for Inter Partes Review of U.S. Pat. No. 8,431,163," dated Jan. 5, 2015, 59 pages.
*Mallinckrodt Hosp. Prods. IP Ltd. v. Praxair Distrib., Inc.*, No. 15-170-GMS, Praxair's Opening Claim Construction Brief Regarding U.S. Pat. No. 8,846,112, filed on Mar. 17, 2016, 1-50.
*Mallinckrodt Hosp. Prods. IP Ltd. v. Praxair Distrib., Inc.*, No. 15-170-GMS, Praxair's Responsive Claim Construction Brief Regarding U.S. Pat. No. 8,846,112, filed on Apr. 14, 2016, 1-48.
Cardinal Intellectual Property, Patent Search Report, dated May 12, 2014, 17 pages.
Rabkin et al., "Nitric Oxide for the Treatment of Postpneumonectomy Pulmonary Edema," Ann. Thorac. Surg,, 2001, 72: 272-4.
Resolucion De Autorizacion De Comercializacion Del Medicamento Vasokinox 450 ppm mol/mol, gas para inhalacion en cilindro, n 69773, dated May 5, 2008, 39 pages.
Review of Parveen Khilnani, Practical Approach to Pediatric Intensive Care, Retrieved from the Internet: URL<www.archdischild.com>, 2005, p. 280.
Rich et al., "Inhaled Nitric Oxide for Cardiac Disease," Respir. Care, 1999, 44(2): 196-202.
Rimensberger et al., "Inhaled nitric oxide versus aerosolized iloprost in secondary pulmonary hypertension in children with congenital heart disease: vasodilator capacity and cellular mechanisms", Circulation, 2001, 103: 544-48.
Roberts et al., "Inhaled Nitric Oxide in Congenital Heart Disease," Circulation, 1993, 87(2): 447-453.
Roofthooft et al., "Persistent Pulmonary Hypertension of the Newborn with Transposition of the Great Arteries," Ann. Thorac. Surg., 2007, 83: 1446-50.
Rosales et al., "Adverse hemodynamic effects observed with inhaled nitric oxide after surgical repair of total anomalous pulmonary venous return," Pediatr. Cardiol., 1999, 20:224-26.

(56) References Cited

OTHER PUBLICATIONS

Rosenzweig et al., "Pulmonary arterial hypertension in children," Pediatr. Pulmonol., 2004, 38: 2-22.
Royster et al., "Differences in Pulmonary Artery Wedge Pressures Obtained by Balloon Inflation Versus Impaction Techniques," Anesthesiology, 1984, 61: 339-341.
Rubanyi, "Pathophysiology and Clinical Applications of Nitric Oxide," Harwood Academic Publishers, Endothelial Cell Research Series, Part B, 1989, 9 pages.
Rubin et al., "Evaluation and Management of the Patient with Pulmonary Arterial Hypertension," Ann. Intern. Med., 2005, 143: 282-292.
Russell et al., "The Effects of Inhaled Nitric Oxide on Postoperative Pulmonary Hypertension in Infants and Children Undergoing Surgical Repair of Congenital Heart Disease," Anesthesia & Analgesia, Jul. 1998, 87(1): 46-51.
S&P Capital IQ, Praxair Distribution, Inc., Private Company Profile, created Apr. 13, 2016, 1 page.
Sample, "Technology today: Left ventricular assist devices," Retrieved from the Internet: URL≤http://www.modernmedicine.com/modern-medicine/content/technology-today-left-ventricle . . . >, Nov. 2005, 6 pages.
Schannwell et al., "Diagnostics in Pulmonary Hypertension," Journal of Physiology and Pharmacology, 2007, 58(Suppl 5): 591-602.
Scherrer et al., "Inhaled Nitric Oxide for High-Altitude Pulmonary Edema," NE J. Med., Mar. 7, Mar. 7, 1996, 334(10): 624-629.
Schreiber et al., "Inhaled Nitric Oxide in Premature Infants with the Respiratory Distress Syndrome," N. Engl. J. Med., 2003, 349: 2099-107.
Sekar, "Inhaled nitric oxide in term and preterm infants," Journal of Perinatology, 2006, 26: S4-S7.
Semigran et al., "Hemodynamic Effects of Inhaled Nitric Oxide in Heart Failure," JACC, Oct. 1994, 24(4): 982-988.
Senni et al., "Heart Failure With Preserved Systolic Function: A Different Natural History?," Journal of the American College of Cardiology, 2001, 38(5): 1277-1282.
Ter Horst et al., "Inhaled nitric oxide attenuates pulmonary inflammation and fibrin deposition and prolongs survival in neonatal hyperoxic lung injury," Am. J. Physiol. Lung Cell Mol. Physiol., 2007, 293: L35-L44.
Simonneau et al., "Clinical Classification of Pulmonary Hypertension," J. Am. Coll. Cardiol., 2004, 43(12 Suppl S): 5S-12S.
Simonneau et al., "Updated Clinical Classification of Pulmonary Hypertension," J. Am. Coll. Cardiol., 2009, 54(1 Suppl): S43-54.
Simonneau et al., "Updated Clinical Classification of Pulmonary Hypertension," J. Am. Coll. Cardiol., 2013, 62(25 Suppl): D34-41.
Stedman's Medical Dictionary at a Glance, 28th Ed, Lippincott Williams & Wilkins © 2006, p. 359.
Stork et al., "Inhaled Nitric Oxide in Full-Term and Nearly Full-Term Infants with Hypoxic Respiratory Failure," Feb. 27, 1997, 336(9): 597-604.
Subhedar et al., "Changes in oxygenation and pulmonary haemodynamics in preterm infants treated with inhaled nitric oxide," Archives of Disease in Childhood, 1997, 77:F191-F197.
Subhedar et al., "Is nitric oxide effective in preterm infants?" Arch. Dis. Child Fetal Neonatal Ed., 2007, 92: 337-341.
Subhedar et al., "Open randomised controlled trial of inhaled nitric oxide and early dexamethasone in high risk preterm infants," Archives of Disease in Childhood, 1997, 77: F185-F190.
Sugimoto et al., "Echocardiographic estimation of pulmonary capillary wedge pressure using the combination of diastolic annular and mitral inflow velocities," J. Echocardiogr., 2013, 11: 1-8.
Sussman et al., "Successful Liver Transplantation Following Medical Management of Portopulmonary Hypertension," A Single-Center Series: American Journal of Transplantation, 2006, 6: 2177-2182.
Truog, "Inhaled Nitric Oxide: A Tenth Anniversary Observation," Pediatrics, 1998, 101: 696.
Turanlahti et al., "Nitric oxide, oxygen, and prostacyclin in children with pulmonary hypertension," Heart, 1998, 79: 169-174.
Van Meurs et al., "Inhaled Nitric Oxide for Premature Infants with Severe Respiratory Failure," N. Engl. J. Med., 2005: 353: 13-22.
Vonbank et al., "Controlled prospective randomised trial on the effects on pulmonary haemodynamics of the ambulatory long term use of nitric oxide and oxygen in patients with severe COPD," Thorax, 2003, 58: 289-293.
Waldmann et al., Oxford Desk Reference Critical Care, Oxford University Press, 2008, 1-4.
Ware, "Inhaled Nitric Oxide in Infants and Children," Crit. Care Nurs. Clin. North Am., Mar. 2002, 14(1): 1-6.
Webster's II New College Dictionary, Houghton Mifflin Company, © 1995, p. 194.
Wessel, "Current and future strategies in the treatment of childhood pulmonary hypertension," Progress in Pediatric Cardiology, 2001, 12: 289-318.
Wessel, "Commentary: Simple Gases and Complex Single Ventricles," J. of Thoracic and Cardiovascular Surgery, Sep. 1996, 112:3 655-57.
Widlitz et al, "Pulmonary arterial hypertension in children," European Respiratory Journal, Jan. 2003, 1-47.
Yamashita et al., "Resistance to Endotoxin Shock in Transgenic Mice Overexpressing Endothelial Nitric Oxide Synthase," Circulation, 2000, 101: 931-937.
Ziegler et al., "Effects of Dipyridamole and Inhaled Nitric Oxide in Pediatric Patients with Pulmonary Hypertension," Am. J. Respir. Crit. Care Med., 1998, 158: 1388-1395.
Zile et al., "New Concepts in Diastolic Dysfunction and Diastolic Heart Failure: Part I—Diagnosis, Prognosis, and Measurements of Diastolic Function," Circulation, Mar. 19, 2002, 105: 1387-1392.
Zile et al., "New Concepts in Diastolic Dysfunction and Diastolic Heart Failure: Part II—Causal Mechanisms and Treatment," Circulation, 2002, 105: 1503-1508.
INOvent delivery system Operation and Maintenance Manual; [online] retrieved on Nov. 20, 2017 from: http://rtasap.com/ppt/inovent.pdf; Feb. 8, 2000; 12 pages. (Year: 2000).
U.S. Non-Final Office Action in U.S. Appl. No. 14/325,993, dated Dec. 16, 2014, 18 pages.
U.S. Final Office Action in U.S. Appl. No. 14/325,993, dated May 18, 2015, 25 pages.
U.S. Non-Final Office Action in U.S. Appl. No. 14/325,993, dated Jan. 19, 2016, 39 pages.
U.S. Final Office Action in U.S. Appl. No. 14/325,993, dated Nov. 28, 2016, 26 pages.
Johns Hopkins University, "Inhaled Nitric Oxide in Preterm Infants", AHRQ Publication No. 11-E001, Oct. 2010, pp. 1-315.
INO Therapeutics INOMAX-nitric oxide gas Highlights of Prescribing Information, 2 pages, published 1999.
Modi et al., "Inhaled nitric oxide in premature neonates," Lancet, vol. 354, p. 2162, Dec. 18, 1999.
Van Meurs et al., "A randomized trial of early versus standard inhaled nitric oxide therapy in term and near-term newborn infants with hyopix respiratory failure," Pediatrics, 113, pp. 559-564, Mar. 3, 2004.
Office Action in corresponding Canadian Patent Application No. 2,855,261, dated Feb. 1, 2018, pp. 1-3.
Office Action in corresponding U.S. Appl. No. 14/313,767, dated Feb. 8, 2018, pp. 1-12.
U.S. Final Office Action in U.S. Appl. No. 14/313,767, dated Oct. 7, 2019, 19 pages.
U.S. Non-Final Office Action in U.S. Appl. No. 14/313,767, dated Dec. 18, 2018, 14 pages.

* cited by examiner

METHODS OF REDUCING THE RISK OF MORTALITY ASSOCIATED WITH A MEDICAL TREATMENT

CLAIM OF PRIORITY

This application is a divisional and claims priority to U.S. application Ser. No. 14/313,767, filed on Jun. 24, 2014, which claims priority under 35 USC § 119(e) to U.S. Patent Application Ser. No. 61/839,352, filed on Jun. 25, 2013. The entire contents of both applications are hereby incorporated by reference.

TECHNICAL FIELD

The present invention relates to methods for reducing the incidence of mortality in infants undergoing medical treatment.

BACKGROUND

Bronchopulmonary dysplasia (BPD) is a chronic lung disease (CLD) of pre-term neonates, attributable to lung immaturity with associated surfactant deficiency, systemic inflammation, and the adverse effects of ventilator and supplemental oxygen therapy for acute respiratory problems. BPD is defined clinically as the need for supplemental oxygen at 36 weeks' postmenstrual age (PMA) (±3 days). There are an estimated 10,000 to 15,000 pre-term neonates diagnosed with BPD in the United States (US) each year. The risk of developing BPD is related to the degree of prematurity, with the highest risk of BPD occurring in pre-term neonates born prior to 26 weeks gestation and ≤750 g body weight at birth. Pre-term neonates who develop BPD may consequently need long-term breathing support, such as with the use of nasal continuous positive airway pressure (NCPAP) machines or ventilators. Prediction of which pre-term neonates are considered to be at risk of developing BPD can be done by standard methods, e.g., as described in Laughon et al., (2011) Am J Respir Crit Care Med 183: 1715-1722.

BPD can develop for several reasons. Pre-term neonates—especially those who develop respiratory distress syndrome (RDS)—frequently require supplemental oxygen therapy (oxygen given through nasal prongs, a mask, or a breathing tube). Preterm neonates with RDS require mechanical ventilation, but over-ventilation of this patient population often results in BPD, due to injury to the lungs. See Northway et al., (1967) New Engl J Med 276:357-368. Infections that occur before or shortly after birth also can contribute to BPD. Lack of lung maturation can also affect a pre-term neonate's chance of developing BPD. Pre-term neonates as young as 22 weeks gestational age are surviving, but generally exhibit immature lungs, with large and simplified alveoli with dysmorphic capillaries, negligible airway epithelial lesions, and mild interstitial fibroproliferation. The younger the pre-term neonate, the less-developed are his or her lungs, leaving him or her more likely to develop BPD.

Pre-term neonates with BPD are at greater risk for poor developmental outcomes, acute and chronic lung disease, an increased susceptibility to infections, and more frequent hospitalization for respiratory illness during the first year of life. Antenatal infections, such as chorioamnionitis and acquired pneumonias, are additional potentially complicating and contributing factors in the development of BPD. Late clinical sequelae of BPD result in recurrent respiratory hospitalizations (50% in the first year) and frequent emergency room visits, pulmonary hypertension, late asthma and structural airway disease, exercise intolerance, apnea, sudden death, systemic hypertension, left ventricular hypertrophy, growth failure, feeding difficulties, and developmental delays.

Currently, there are no approved medicinal products in the US or globally to prevent the development of BPD in pre-term neonates. Following FDA approval of inhaled nitric oxide (a potent and selective pulmonary vasodilator) for the treatment of pulmonary hypertension secondary to hypoxic respiratory failure (HRF) in the term/near term neonate, it has been suggested that inhaled nitric oxide might also benefit the sick pre-term neonate and, in particular, reduce the incidence and/or severity of BPD. Radiographic evidence suggests prolonged inhaled nitric oxide therapy improves lung vascular growth after VEGF inhibition and improves alveolarization in experimental BPD in preterm lambs. The potential therapeutic targets for the use of inhaled nitric oxide in the pre-term neonate include: improved gas exchange and reduced $FiO_2$, lower pulmonary artery pressure, anti-inflammatory and antioxidant effects, sustained surfactant production, and preservation or stimulation of angiogenesis and alveolarization in the developing lung.

Several studies have been directed to use of inhaled nitric oxide to prevent (reduce the incidence of) BPD.

Kinsella et al., (1999) Lancet 354:1061-1065, was a randomized, double-blind, placebo-controlled, multi-center study in 80 pre-term neonates that was terminated early for enrollment issues. Inhaled nitric oxide was administered at a dose of 5 ppm for 7 days. The results of this study demonstrated a 15.4% reduction in death or BPD (77% inhaled nitric oxide vs 91% placebo; p=0.14), with no increase in severe intraventricular haemorrhage (IVH).

Schreiber et al., N Engl J Med (2003) 349:2099-2107, was a randomized, double-blind, placebo-controlled, single-center study in 207 pre-term neonates administered a starting dose of inhaled nitric oxide 10 ppm for 1 day, then 5 ppm for 6 days. The results of the Schreiber study demonstrated a 24% reduction in CLD/death (48.6% inhaled nitric oxide vs 63.7% placebo; p=0.03), a 47% reduction in severe IVH/PVL (PVL=periventricular leukomalacia) (12.4% inhaled nitric oxide vs 23.5% placebo; p=0.04), and a 47% reduction in "abnormal or delayed" development (p=0.01).

Van Meurs et al., Pediatrics (2004) 113:559-564, was a randomized, double-blind, placebo-controlled, multi-center study in 420 (800 planned) pre-term neonates. Inhaled nitric oxide was administered at a starting dose of 5 ppm and increased to 10 ppm if no response (Mean 3 days therapy). The study was stopped prematurely. The results of this study showed overall no difference vs placebo in death or BPD and no difference in IVH.

Kinsella et al., N Engl J Med (2006) 355:354-364, designated the "INOT 25" study, was a randomized, double-blind, placebo-controlled, multi-center study in 793 subjects. Inhaled nitric oxide was administered at a dose of 5 ppm while the patient was intubated, with a median treatment duration of 14 days. The results of the INOT 25 study showed overall no difference vs placebo in CLD or death (71.6% vs 75.3%) and a 27% reduction in IVH/PVL (17.5% vs 23.9%).

Mercier et al., Lancet (2010) 376:346-54, designated the "INOT 27" study, was a randomized, double-blind, placebo-controlled, multi-center study in 35 centers in nine European Union countries (800 subjects). Inhaled nitric oxide was administered at a dose of 5 ppm for 7-21 days (treatment duration Mean 16.3 days). The results of the INOT 27 study showed overall no difference in survival without BPD at 36 weeks postmenstrual age (placebo 65.5% vs inhaled nitric oxide 65% (p=0.73)).

Ballard et al., N Engl J Med (2007) 357:1444-1445, and Ballard et al., N Engl J Med (2006) 355:343-353, report a randomized, double-blind, placebo-controlled, multicenter study in which 537 pre-term neonates received either inhaled nitric oxide or placebo. Therapy was initiated between Day 7 and Day 21. Patients were administered inhaled nitric oxide 20 ppm for 2 to 4 days, then stepped-down in weekly intervals. All patients were treated for 24 days. The results of this study showed a 20% improvement in survival without CLD at 36 weeks postmenstrual age with inhaled nitric oxide (inhaled nitric oxide 43.9% vs placebo 36.8%, p=0.042). Patients were discharged (p=0.04) or off all ventilator support sooner on study drug (40 weeks, inhaled nitric oxide 65% vs placebo 53%, p=0.01; 44 weeks, inhaled nitric oxide 82% vs placebo 76%, p=0.03).

SUMMARY

It has now been discovered that a particular subset of patients is at an increased risk of mortality when treated with inhaled nitric oxide, and that this subset is defined in part by one or more of race, gender, and gestational age, and also by determination of risk of developing BPD. The affected subset of patients is white, male, pre-term neonates; more specifically, white, male, pre-term neonates less than 27 weeks gestational age; and even more specifically, white, male, pre-term neonates less than 27 weeks gestational age that are at risk of developing BPD. The same risk was not observed in pre-term neonates (male or female) of other races, specifically American Indian/Alaska Native, Asian, black, and Hispanic pre-term neonates, nor in female pre-term neonates of any race (including white), nor in neonates of gestational age greater than 27 weeks. Non-white pre-term neonates as a class and female pre-term neonates as a class, even those of gestational age less than 27 weeks, were able to safely receive inhaled nitric oxide administered as a means to prevent development of BPD. The newly discovered risk can be described as follows: in white males<27 weeks gestational age, inhaled nitric oxide may have an increased risk of death as compared to other subgroups. Another way to describe the risk is: in white male pre-term infants<27 weeks gestational age, without pulmonary hypertension and at risk of developing BPD, inhaled nitric oxide may have an increased risk of death as compared to other subgroups. There was seen in one study an imbalance in deaths in this subgroup when treated with nitric oxide as compared to placebo at doses of 20 ppm for 3 days reduced to 10 ppm for 10 days and 5 ppm for remainder of 24 days. This was not seen in other subgroups.

In one aspect, the invention is directed to a method of treatment that includes identifying a plurality of neonates (i.e., two or more) as being candidates for treatment with inhaled nitric oxide (preferably for a reason—such as prevention of BPD—other than treatment of a condition involving pulmonary hypertension); determining that the race of a first neonate of the plurality is black or another non-white race such as American Indian/Alaska Native, Asian, or Hispanic; administering inhaled nitric oxide to the first neonate; determining that the race of a second neonate of the plurality is white; determining that the gender of the second neonate is male; determining that the second neonate is of less than 27 weeks gestational age; determining that the fact that the second neonate is a white male of less than 27 weeks gestational age means the second neonate is at a higher risk of mortality upon administration of inhaled nitric oxide compared to a black (or other non-white) male neonate or a female neonate of the same gestational age; and excluding the second neonate from treatment with inhaled nitric oxide, based on the determination that the second neonate has the higher risk of mortality. Thus, neonates who are determined not to have that higher risk of mortality (e.g., because they are non-white, or are female, or are not less than 27 weeks gestational age) are treated with inhaled nitric oxide, while those who have the higher risk of mortality are not treated with inhaled nitric oxide. The reason that the neonates are candidates for treatment with inhaled nitric oxide may be that they are at risk for developing BPD. The reason is preferably not that the neonates have a condition associated with pulmonary hypertension, since such a condition may itself be acutely life-threatening and, in the judgment of the physician, require treatment with inhaled nitric oxide even where the neonate is a white male of less than 27 weeks gestational age. Thus, a further determination that may be made prior to deciding not to treat with inhaled nitric oxide is that the neonate does not have pulmonary hypertension.

In another aspect, the second neonate is identified (e.g., diagnosed) as being at risk of incurring BPD, e.g., from damage attributable to supplemental oxygen therapy that is frequently given to pre-term neonates. Such a neonate may be excluded from treatment of inhaled nitric oxide at a dosing regimen typically used to prevent BPD because of the mortality risk specific to white, male, pre-term neonates of less than 27 weeks gestational age.

Administration of inhaled nitric oxide to pre-term neonates who are candidates for inhaled nitric oxide therapy because they have been identified as being at risk for developing BPD typically begins no less than five days after birth, due at least in part to risk of brain hemorrhage. Treatment of these pre-term neonates may begin at a point during the period that is 5 to 14 days after birth, 5 to 10 days after birth, 5 to 21 days after birth, 7 to 21 days after birth, or 5 to 7 days after birth. Administration of inhaled nitric oxide for the purpose of preventing BPD in susceptible pre-term neonates generally continues for 20-30 days after it is initiated. In specific treatment protocols, administration of inhaled nitric oxide may be continued for at least 18 days, 19 days, 20 days, 21 days, 22 days, 23 days, 24 days, 25 days, 26 days, 27 days, 28 days, 29 days or 30 days, and may involve a stepwise decrease in nitric oxide concentration (e.g., in two, three, or four steps) over that time period. Treatments requiring inhaled nitric oxide for prevention or treatment of a different disorder or underlying condition may have a different dosing regimen.

The second neonate may have an underlying condition, such as pulmonary hypertension or hypoxic respiratory failure, that may benefit from inhaled nitric oxide treatment at a very different dosing regimen than suggested for prevention of BPD. Thus, in one aspect, a neonate who is male, white, less than 27 weeks gestational age, and at risk of BPD may indeed safely receive inhaled nitric oxide for the underlying condition, but for a limited duration less than that typically utilized to prevent BPD (e.g., a limited duration of approximately one, two, three, four, five, or six hours, 12 hours, 18 hours, 24 hours, 36 hours, 48 hours, three days, or four days). The duration will typically be long enough to relieve, at least temporarily, the underlying condition, but will usually be less than 96 hours (e.g., less than 80 hours, or less than 70 hours, or less than 60 hours. In some embodiments, the treatment will last for a period between approximately 40 hours and 70 hours.

One or more of the neonates may have, or be at risk of incurring, pulmonary hypertension that can be relieved at least in part with inhaled nitric oxide at a specific dosing regimen (timing, duration, amount, and manner of dosing) different from that typically used to prevent BPD. The second neonate may be given an alternate acceptable treatment for his/her underlying condition. The second neonate may also be at risk of mortality due to an underlying condition, such pulmonary hypertension, and may be administered inhaled nitric oxide at a specific dosing regimen that is different (much shorter duration) from the dosing regimen that is used for the prevention of BPD. If the underlying condition is hypoxic respiratory failure, the alternate treatment could be, for example, ventilatory support (e.g., high-frequency oscillatory ventilation) with supplemental oxygen, extracorporeal membrane oxygenation (ECMO), intravenous fluids, surfactant, and/or bicarbonate therapy. In some embodiments, the first and/or second neonate is a potential candidate for inhaled nitric oxide at least in part because he/she is identified as being at risk of BPD. In other embodiments, the first and/or second neonate is a candidate for inhaled nitric oxide because the neonate has a condition that can lead to pulmonary hypertension, or is undergoing, or has just undergone, a procedure that can lead to pulmonary hypertension, such as cardiac surgery involving heart/lung bypass.

In another aspect, the method of treatment includes identifying a plurality of neonates as being candidates for treatment with inhaled nitric oxide; determining that the race of a first neonate of the plurality is black or another non-white race or that the gender of the first neonate is female; administering inhaled nitric oxide to the first neonate; determining that the race of a second neonate of the plurality is white; determining that the gender of the second neonate is male; determining that the fact that the second neonate is a white male means the second neonate is at a higher risk of mortality upon administration of inhaled nitric oxide compared to a nonwhite (e.g., black) or female neonate of the same gestational age; and excluding the second neonate from treatment with inhaled nitric oxide, based on the determination that the second neonate has the higher risk. In some embodiments, the neonate is less than 27 week gestational age and/or is at risk of developing BPD. One or more of the neonates may have, or be at risk of incurring, pulmonary hypertension that can be relieved at least in part with inhaled nitric oxide. The second neonate may be given an alternate acceptable treatment (or inhaled nitric oxide at a specific dosing regimen dissimilar from the dosing regimen that would typically be used to prevent BPD) for his/her underlying condition. If the underlying condition is pulmonary hypertension or hypoxic respiratory failure, the second neonate may be given one or more alternate acceptable treatment(s), such as ventilatory support (e.g., high-frequency oscillatory ventilation) with supplemental oxygen, ECMO, intravenous fluids, surfactant, and/or bicarbonate therapy, instead of inhaled nitric oxide. In other embodiments, the second neonate is a candidate for inhaled nitric oxide at a specific dosing regimen different than the dosing regimen administered to the first neonate for prevention of BPD because he has a condition that can lead to pulmonary hypertension, or is undergoing, or has just undergone, a procedure that can lead to pulmonary hypertension, such as cardiac surgery involving heart/lung bypass. In this instance, the dosing regimen of inhaled nitric oxide received by the second neonate is for a shorter duration than would typically be used to prevent BPD.

In another aspect, the method of treatment includes performing at least one diagnostic process (which may include performing echocardiography) to identify a plurality of neonates who have an underlying condition, such as hypoxic respiratory failure or being at risk of BPD, that makes them candidates for inhaled nitric oxide treatment; determining that the race of a first neonate of the plurality is black (or another non-white race) or the gender is female; administering inhaled nitric oxide to the first neonate; determining that a second neonate of the plurality is a white male of less than 27 weeks gestational age; determining that the fact that the second neonate is a white male of less than 27 weeks gestational age means the second neonate is at a higher risk of mortality upon administration of inhaled nitric oxide compared to a black or female neonate patient of the same gestational age; and either providing an alternative treatment to the second neonate or administering inhaled nitric oxide at a shorter duration than what would typically be used for prevention of BPD. Such duration for the second neonate may be less than 1 day, 1 day, 2 days, 3 days, or 4 days, or an increment of hours that is less than 96 hours, e.g., 6 hours, 12 hours, 18 hours, 24 hours, 36 hours, 40 hours, 48 hours, 50 hours, 60 hours, 72 hours, or 84 hours. The second neonate may be given an alternate acceptable treatment for his underlying condition, such as one or more of ventilatory support (e.g., high-frequency oscillatory ventilation) with supplemental oxygen, ECMO, intravenous fluids, surfactant, and/or bicarbonate therapy, instead of inhaled nitric oxide.

Also within the invention is a method of selecting a treatment for a neonate, the method encompassing performing at least one diagnostic process (which may include echocardiography) to identify a neonate (e.g., a premature infant of less than 27 weeks gestational age who may be at risk of BPD) with pulmonary hypertension and/or hypoxic respiratory failure; determining that the neonate is a white male; determining that the fact that the neonate is a white male means he is at a higher risk of mortality upon administration of inhaled nitric oxide compared to a black or other non-white neonate or a female neonate of the same gestational age when administered inhaled nitric oxide in a fashion consistent with preventing BPD; and either excluding the white male neonate from treatment with inhaled nitric oxide or treating the white male neonate with inhaled nitric oxide at a dosing regimen of a significantly shorter duration than the 20-30 days that would typically be used for preventing BPD in pre-term neonates susceptible to BPD, based on the determination that the white male neonate is at a higher risk of mortality than a black neonate or female neonate of the same gestational age if treated with a dosing regimen suitable for preventing BPD. Alternatives to treatment with inhaled nitric oxide for treating or preventing hypoxic respiratory failure or pulmonary hypertension may include one or more of ventilatory support (e.g., with supplemental oxygen), ECMO, intravenous fluids, surfactant, and/or bicarbonate therapy or other acceptable treatment. The ventilatory support may involve high-frequency oscillatory ventilation. In some embodiments, the white male neonate is considered to be at risk of BPD. In other embodiments, the neonate is a candidate for inhaled nitric oxide because he has a condition that can lead to pulmonary hypertension, or is undergoing, or has just undergone, a procedure that can lead to pulmonary hypertension, such as cardiac surgery involving heart/lung bypass.

Also within the invention is a method of selecting a treatment for a pre-term neonate, the method encompassing identifying a pre-term neonate of less than 27 weeks gestational age; treating the pre-term neonate with mechanical ventilation or positive airway pressure support; determining that the pre-term neonate is at risk of BPD; determining that the pre-term neonate is a white male; determining that the fact that the pre-term neonate is a white male means the pre-term neonate is at a higher risk of mortality upon administration of inhaled nitric oxide for prevention of BPD compared to a black or other non-white pre-term neonate or a female pre-term neonate of the same gestational age; and, based on the determination of higher risk, excluding the white, male, pre-term neonate from treatment with inhaled nitric oxide for prevention of BPD. The white, male, pre-term neonate may be treated with high-frequency oscillatory ventilation instead of inhaled nitric oxide.

In another aspect, the method of treatment includes identifying a pre-term neonate of less than 27 weeks gestational age as being in need of treatment for prevention of BPD; determining that the race of the pre-term neonate is white and the gender is male; determining that the fact that the pre-term neonate is a white male means the pre-term neonate is at a higher risk of mortality upon administration of inhaled nitric oxide compared to a black or other non-white pre-term neonate or a female pre-term neonate of the same gestational age; deciding to postpone inhaled nitric oxide treatment until the white, male, pre-term neonate reaches 27 weeks postmenstrual age; administering a treatment other than inhaled nitric oxide to the white, male, pre-term neonate; and, when the white, male, pre-term neonate reaches 27 weeks postmenstrual age, beginning administration of inhaled nitric oxide to the white, male, pre-term neonate, where the decision to postpone inhaled nitric oxide treatment until 27 weeks postmenstrual age is based on the higher risk of mortality in white, male, pre-term neonates of less than 27 weeks postmenstrual age. The nitric oxide will typically be administered initially at 20 ppm, and may be decreased gradually to 10 ppm, then 5 ppm, and finally 2 ppm over the course of treatment. The treatment administered prior to beginning inhaled nitric oxide administration may be, for example, ventilatory support (e.g., with supplemental oxygen).

In another aspect, the method of treatment includes identifying a pre-term neonate of less than 27 weeks gestational age (e.g., less than 26 weeks) as being in need of inhaled nitric oxide for prevention or treatment of a condition involving pulmonary hypertension (e.g., hypoxic respiratory failure); determining that the race of the pre-term neonate is white; determining that the gender of the pre-term neonate is male; determining that the fact that the pre-term neonate is a white male means the pre-term neonate is at a higher risk of mortality upon administration of inhaled nitric oxide compared to a black or other non-white pre-term neonate or a female pre-term neonate of the same gestational age; administering a treatment other than inhaled nitric oxide to the white, male, pre-term neonate; and, when the white, male, pre-term neonate reaches 27 weeks postmenstrual age, beginning administration of inhaled nitric oxide to the white, male, pre-term neonate, where the decision to postpone inhaled nitric oxide treatment until 27 weeks postmenstrual age is because of the higher risk of mortality in white, male, pre-term neonates of less than 27 weeks postmenstrual age. The nitric oxide will typically be administered at 20 ppm. The treatment administered prior to beginning inhaled nitric oxide administration may be, for example, ventilatory support (e.g., with supplemental oxygen), ECMO, intravenous fluids, surfactant, and/or bicarbonate therapy, or another alternative therapy. Such treatment (except ECMO) may optionally be continued during the period that inhaled nitric oxide is administered. The ventilatory support may involve high-frequency oscillatory ventilation. Treatment of any pre-term neonate with ECMO may be possible only if the pre-term neonate's blood vessels are of adequate size. In some embodiments, the white, male, pre-term neonate is considered to be at risk of BPD, in addition to having a condition involving pulmonary hypertension. The pre-term neonate may be a candidate for inhaled nitric oxide because he has a condition that can lead to pulmonary hypertension, or is undergoing, or has just undergone, a procedure that can lead to pulmonary hypertension, such as cardiac surgery involving heart/lung bypass.

In another aspect, the method of treatment includes identifying a pre-term neonate of less than 27 weeks gestational age as being a candidate for treatment with inhaled nitric oxide because of an underlying condition; determining that the race of the pre-term neonate is white and the gender is male; providing ventilatory support to the pre-term neonate; determining that the fact that the pre-term neonate is a white male means the pre-term neonate is at a higher risk of mortality upon administration of inhaled nitric oxide compared to a black or other non-white pre-term neonate or a female pre-term neonate of the same gestational age; and, based on the determination of higher risk, either excluding the white, male, pre-term neonate from treatment with inhaled nitric oxide, or treating the white, male, pre-term neonate with inhaled nitric oxide, but using a treatment regimen shorter than typically used to treat the underlying condition. The ventilatory support may be continued after the pre-term neonate is excluded from treatment with inhaled nitric oxide, or may be substituted with ECMO at that point if the underlying condition involves hypoxia and if ECMO is appropriate for the patient. The ventilatory support may be high-frequency oscillatory ventilation. The white, male, pre-term neonate may also be treated with intravenous fluids, surfactant, and/or bicarbonate therapy. In some embodiments, the white, male, pre-term neonate is a candidate for inhaled nitric oxide at least in part because he is identified as being at risk of BPD. In other embodiments, the pre-term neonate is a candidate for inhaled nitric oxide because he has a condition that can lead to pulmonary hypertension, or is undergoing, or has just undergone, a procedure that can lead to pulmonary hypertension, such as cardiac surgery involving heart/lung bypass. Alternatively or in addition, the pre-term neonate may have pulmonary hypertension (e.g., associated with hypoxic respiratory failure) that can be relieved at least in part with inhaled nitric oxide.

In certain embodiments of any of the above methods, the neonates (in particular, the white, male, pre-term neonates) are not dependent on right-to-left shunting of blood, and/or do not have left ventricular dysfunction. The methods may include steps of carrying out standard tests (such as echocardiography) to determine whether the neonates have either or both of those conditions, prior to making a decision about administration of inhaled nitric oxide.

In certain embodiments of the above methods, the non-white neonates and female neonates, and also the white, male neonates who are more than 27 weeks postmenstrual age, who are not excluded from treatment with inhaled nitric oxide (because the above-described increased risk of mortality does not apply to them), are treated with inhaled nitric oxide as a means to prevent BPD. This treatment typically begins at least five days after birth of a pre-term (<30 weeks gestational age) neonate, e.g., five to fourteen days after birth, five to ten days after birth, five to seven days after birth, or five to 21 days after birth. A typical protocol for inhaled nitric oxide treatment of a pre-term neonate at risk of BPD involves administering decreasing concentrations of nitric oxide over the course of administration, beginning at 20 ppm. In certain embodiments, the initial dose of 20 ppm nitric oxide is decreased to 10, then 5, and then 2 ppm over the course of administration. In specific embodiments, the administration of nitric oxide is for at least 20 days, preferably at least 24 days, and can be up to 30 days. In a specific example of nitric oxide administration, the initial administration of 20 ppm nitric oxide lasts for a period of 48 to 96 hours, followed by a week at 10 ppm, a week at 5 ppm, and then a week at 2 ppm.

In certain embodiments, an alternative treatment for a pre-term neonate who is at risk of BPD, but who is not treated with inhaled nitric oxide because the pre-term neonate is a white male of less than 27 weeks gestational age, is one or more of any acceptable treatment, including but not limited to caffeine, vitamin A, supplemental oxygen, and one or more surfactants, antenatal steroid, etc. (Any of these alternative treatments (e.g., vitamin A or supplemental oxygen) may also be used in conjunction with inhaled nitric oxide for the prevention of BPD in appropriate patients.)

The invention also includes a system for use in administering inhaled nitric oxide gas. The system reduces the overall risk of mortality from inhalation of nitric oxide by providing instructions for use of nitric oxide that include a warning about a specific risk to a specific population of pre-term neonates. The system also includes a source of pharmaceutically acceptable nitric oxide gas for inhalation and a delivery device suitable for delivering nitric oxide gas from the source to a neonatal patient. The instructions may include, for example, a description of operating the system to deliver 20 ppm inhaled nitric oxide to treat a condition such as one or more of hypoxic respiratory failure or BPD or pulmonary arterial hypertension, a contraindication for neonates who are dependent on right to left shunting of blood, and/or a contraindication or warning regarding patients who have pre-existing left ventricular dysfunction. The instructions also include a warning that inhaled nitric oxide may produce an increased risk of death in white, male, pre-term infants of less than 27 weeks gestational age (and do not include a similar warning for pre-term infants of less than 27 weeks gestational age who are female or are not white). The latter warning may also specify that the white, male, pre-term infants of less than 27 weeks gestational age are ones who are at risk of developing BPD, may say the white, male, pre-term infants do not have pulmonary hypertension, and may be effective in reducing the overall risk of mortality from inhalation of nitric oxide compared to a similar system without the instructions, and may be effective in excluding a population of white, male, pre-term infants less than 27 weeks gestational age from treatment with inhaled nitric oxide, thereby reducing the overall risk of mortality resulting from inhaled nitric oxide treatment. In addition or instead, the instructions may communicate that, in a subset of white, male, pre-term infants less than 27 weeks gestational age, without pulmonary hypertension and at risk of developing BPD, there was seen in one study an imbalance in deaths in the INOmax treated group as compared to placebo, and may specify that the study used doses of 20 ppm for 3 days reduced to 10 ppm for 10 days and 5 ppm for remainder of 24 days.

In other embodiments, the white male neonate who is excluded is less than 30 weeks gestational age, or less than 29 weeks, 28 weeks, 26 weeks, 25 weeks, 24 weeks, or 23 weeks.

Also disclosed is a method of distributing a pharmaceutical product. This method includes supplying a source of nitric oxide or any material that can be converted to nitric oxide to a medical provider responsible for treating a plurality of neonatal patients who are candidates for treatment with inhaled nitric oxide (e.g., neonates with hypoxic respiratory failure and/or pulmonary hypertension, or those at risk of BPD), including pre-term neonates such as those of less than 27 weeks gestational age; informing the medical provider than a recommended dose of inhaled nitric oxide gas is 20 ppm nitric oxide; and providing a warning to the medical provider that the risk of mortality from inhalation of nitric oxide is higher in white, male, pre-term neonates less than 27 weeks gestational age (e.g., those who are at risk of BPD and so might otherwise be treated with inhaled nitric oxide to help prevent BPD) than in non-white pre-term neonates or female pre-term neonates of the same gestational age. In preferred embodiments, the warning is effective to cause a medical provider considering inhaled nitric oxide treatment in a white, male, pre-term neonate less than 27 weeks gestational age (e.g., for prevention of BPD) to forego use of inhaled nitric oxide in that pre-term neonate in order to avoid putting the pre-term neonate at increased risk of mortality, or otherwise to reduce the use of inhaled nitric oxide in such white, male, pre-term neonates, including those at risk of developing BPD. The medical provider may choose to substitute another appropriate treatment. The various instructions and warnings may be supplied to the medical provider in the form of a label attached to and/or shipped with the source of nitric oxide, or in materials otherwise supplied to the medical provider. The medical provider who is so informed may use the source of nitric oxide (or any material that can be converted to nitric oxide gas that is then delivered to and inhaled by a patient) to treat patients who are candidates for treatment with inhaled nitric oxide, including pre-term neonates. Prior to treating a given pre-term neonate, the medical provider may assess whether the pre-term neonate falls within one of the populations described in the instructions as being at increased risk of harm. This assessment includes determining whether the patient is a white, male, pre-term neonate of less than 27 weeks gestational age, and may include determining whether the patient is at risk of BPD. In accordance with the warning regarding that population, the medical provider will likely avoid treating such a patient with inhaled nitric oxide, and may utilize another suitable alternative treatment instead. If the patient is a non-white or a female, the warning does not apply, so the medical provider can treat such a patient with inhaled nitric oxide, even though the latter patient is of less than 27 weeks gestational age and can be characterized as at risk of BPD.

The method of distributing the pharmaceutical product may also include steps of manufacturing the source of nitric oxide gas before it is supplied to the medical provider. If the source of nitric oxide gas is a cylinder of compressed gas, it may be manufactured by a process comprising diluting nitric oxide gas with nitrogen gas to produce a compressed gaseous mixture of nitric oxide and nitrogen in a cylinder. The pharmaceutical product may instead include $N_2O_4$ (in liquid form) or nitrogen dioxide (in gaseous form); such a product is supplied in a form that is ultimately converted to nitric oxide at the patient's bedside. If the source of nitric oxide gas is a container containing compressed nitric oxide or nitrogen dioxide, the method may further comprise generating the nitric oxide or nitrogen dioxide and introducing it into the container in compressed form, prior to supplying it to the medical provider. By "supplying to the medical provider" is meant causing the source of nitric oxide gas to be delivered to the medical supplier, e.g., by transporting it from one site (such as the manufacturing location or a distributer or storage building) to another site (e.g., where the medical provider administers inhaled nitric oxide treatment to patients).

DETAILED DESCRIPTION

Several exemplary embodiments of the claimed methods and systems are described below. It is to be understood that what is claimed is not limited to the details of set forth in the following description. The methods and systems are capable of other embodiments and of being practiced or being carried out in various ways.

INOmax® (nitric oxide) for inhalation is an approved drug product. The FDA-approved prescribing information for INOmax dated 2013 is attached as Appendix 1, and so forms part of the present disclosure, and also is incorporated by reference herein in its entirety. INOmax® is a selective pulmonary vasodilator, which, in conjunction with ventilatory support or other appropriate agents, is indicated for the treatment of term and near-term (>34 weeks gestation) neonates with hypoxic respiratory failure associated with clinical or echocardiographic evidence of pulmonary hypertension, where it improves oxygenation and reduces the need for extracorporeal membrane oxygenation. The recommended dose of INOmax for the approved indication is 20 ppm, maintained for up to 14 days or until the underlying oxygen desaturation has resolved. Weaning should occur gradually. Adverse reactions per the label include methemoglobinemia and nitrogen dioxide levels, both which can be dose dependent.

Inhaled nitric oxide may be administered via a delivery device such as INOmax DSIR®, INOmax® DS or INOvent®, each of which delivers operator-determined concentrations of nitric oxide in conjunction with a ventilator or breathing gas administration system after dilution with oxygen or an oxygen/air mixture. A nitric oxide delivery system includes a nitric oxide administration apparatus, a nitric oxide gas analyzer and a nitrogen dioxide gas analyzer.

The source of nitric oxide used in any of the presently disclosed methods can be a cylinder of compressed gas containing nitric oxide, typically as a mixture with an inert gas such as nitrogen or helium. Nitric oxide is generated by manufacturing the gases separately, mixing them in an appropriate ratio, and introducing them into an appropriate cylinder under pressure. The mixing may occur in two steps: first diluting bulk nitric oxide with nitrogen to a concentration of, e.g., 5,000 ppm or 28,600 ppm in interim cylinders, and then diluting that mixture further by introducing the mixture into the final cylinders and filling them with more nitrogen to produce a concentration of, e.g., 100 ppm or 800 ppm in the final cylinders. Care is taken not to introduce any water or oxygen into the cylinders. The cylinders are equipped with an appropriate valve, shipped to the point of use, and attached to a delivery device (as described above) to facilitate inhalation of the gas by the patient.

The source of nitric oxide can instead be a nitric oxide-generating device that generates nitric oxide from a suitable nitrogen source, such as air (see for reference U.S. Pat. No. 5,396,882, incorporated herein by reference) or nitrogen dioxide. The source of nitrogen dioxide can be, for example, a canister of compressed nitrogen dioxide gas or a container of $N_2O_4$ (which, when treated under appropriate conditions, will give off nitrogen dioxide). Manufacturing a source of nitrogen dioxide includes steps of compressing nitrogen dioxide gas into a suitable container or introducing $N_2O_4$ in liquid form into a suitable container. The container is supplied in a device that includes a filter containing a reducing agent or antioxidant, such as ascorbic acid, which reduces the nitrogen dioxide to form nitric oxide at the patient's bedside. At the point of administration, such a nitric oxide-generating device is typically attached to a gas-delivery device (such as a ventilator) to facilitate inhalation of the newly formed nitric oxide gas by the patient.

Inhaled nitric oxide is contraindicated in the treatment of neonates known to be dependent on right-to-left shunting of blood.

Patients with left ventricular dysfunction who are treated with nitric oxide may experience pulmonary edema, increased pulmonary capillary wedge pressure, worsening of left ventricular dysfunction, systemic hypotension, bradycardia and cardiac arrest. If this occurs, the medical provider is advised to discontinue inhaled nitric oxide while providing symptomatic care. The medical provider may choose to forego use of inhaled nitric oxide altogether in patients who are determined to have pre-existing left ventricular dysfunction, or may administer inhaled nitric oxide while monitoring carefully for adverse events related to the left ventricular dysfunction (such as pulmonary edema), and discontinuing use of the gas only if necessary.

"Neonate" or "neonatal" refers to an infant within 4 weeks of birth.

"Pre-term neonate" or "preterm neonate" refers to a neonate who is less than 34 weeks gestational age.

Despite multiple trials indicating the safety of inhaled nitric oxide in full-term, near-term, and pre-term neonates (several clinical trials in the latter group are summarized in the "Data Review and Bibliography—Use in Premature Neonates" document attached as Appendix 2, which forms part of the present disclosure and also is incorporated by reference in its entirety), it has been unexpectedly discovered that there is a specific neonatal patient population that is at increased risk of mortality (i.e., death) if treated with inhaled nitric oxide, compared to the same population that does not receive inhaled nitric oxide. The increased mortality rate was unexpectedly observed in white, male, pre-term neonates of gestational age less than 27 weeks who were being treated with inhaled nitric oxide because they were at risk of BPD, on the theory that inhaled nitric oxide may be useful in preventing (reducing the incidence of) BPD. The increased mortality rate was not observed in non-white, male pre-term neonates of gestational age less than 27 weeks, or in female pre-term neonates of any race who were of the same gestational age. Once an individual white, male pre-term neonate born at less than 27 weeks gestation age reaches a point corresponding to 27 weeks postmenstrual age and at least 5 days after birth, he can safely receive inhaled nitric oxide.

Alternative preventative treatments for white, male, pre-term neonates initially identified as candidates for inhaled nitric oxide treatment intended for the prevention of BPD, but who are now excluded from that preventative treatment because of the newly discovered risk of mortality, include one or more of caffeine, vitamin A, supplemental oxygen, and/or surfactant. Oxygen is generally administered at 21-60% of the inhaled gas, but can be administered at a higher level if necessary. It is considered to be supplemental oxygen if the patient's inhalation gas contains a level of oxygen higher than in air, i.e., at least 22% oxygen (e.g., 22-60%), and up to 90%, 99% or even 100% oxygen. Caffeine therapy can be, e.g., 20-25 mg/kg every 24 hours as citrate orally or IV (intravenous) over 10 minutes, beginning 24 hours after loading dose. Alternatively, 18-30 mg/kg every 12 or more hours may be administered. Vitamin A therapy includes, for example, 7,500-15,000 IU intramuscularly daily for up to 10 days. Surfactant treatment generally depends on the type of surfactant being administered, but is typically administered in three doses: first dose is 3 cc/kg, then if $FiO_2$ (fraction of inspired oxygen) six hours after the first dose is greater than 60%, the second dose of 3 cc/kg is administered. If $FiO_2$ six hours after the second dose is greater than 40%, then the third dose of 3 cc/kg is administered.

Certain risk calculators may be used to assist in identifying if a patient is at risk of BPD. Risk calculator software known in the art may take into account a pre-term neonate's gestational age, weight and ventilator support needs, among other factors. Such a risk calculator may help a clinician or therapist to assist in determining if a given pre-term neonate is at risk of developing BPD. See, e.g., Laughon et al., (2011) Am J Respir Crit Care Med 183:1715-1722.

As in other situations where the race of the patient has an effect on treatment options, determining whether the patient is white or non-white is generally accomplished by visual assessment coupled with querying the patient's parent or other relative, and/or reviewing the patient's records. Self-identification of the patient's race by the patient's biological mother or father is typically the means by which race is determined for this purpose. Biological markers (such as genetic markers) indicative of race may also be useful, where such markers have been validated as accurate predictors of whether a patient is white vs. non-white. As the heightened risk in white males, compared to non-white males, is theorized to be due to a recessive trait present in white males and not in non-white males, a male pre-term neonate of mixed white and non-white ancestry is (according to this theory) likely to carry the dominant trait that is protective in non-whites. Thus, if there is a question as to how to categorize a male pre-term neonate of mixed white and non-white ancestry for purposes of the presently claimed methods, a physician may choose to categorize the pre-term neonate as non-white and thus eligible for treatment with inhaled nitric oxide.

In general, administration of inhaled nitric oxide to pre-term neonates that have been identified as at risk for developing BPD and/or as likely to have a therapeutic response to the inhaled nitric oxide should begin no less than five days after birth. Treatment of these pre-term neonates may begin at some point within the period of 5 to 14 days after birth, 7 to 21 days after birth, 5 to 21 days after birth, or 5 to 7 days after birth. Administration of inhaled nitric oxide for this purpose generally continues for 20-30 days after it is initiated. In specific treatment protocols, administration of inhaled nitric oxide may be continued for at least 20 days, 21 days, 22 days, 23 days, 24 days, 25 days, 26 days, 27 days, 28 days, 29 days or 30 days.

EXAMPLES

A multi-center, double blind, placebo-controlled randomized clinical trial designated the "BPD-301" study was conducted to examine the efficacy of inhaled nitric oxide in preventing BPD in preterm neonates less than 30 weeks gestational age and less than 1250 grams who required mechanical ventilation or positive pressure support. Patients were identified as (1) American Indian or Alaska Native, (2) Asian, (3) Black, (4) Hispanic, (5) White, or (6) Other. Continuous inhaled nitric oxide or placebo gas administration into the inspiratory limb of the ventilator circuit in the mechanically ventilated subject was accomplished using an INOvent® delivery device. The placebo group received the same dose of nitrogen that the active or treatment group received of inhaled nitric oxide. Administration of inhaled nitric oxide or placebo was begun at a point during the window of time 5 to 14 days after the subject's birth and continued for 24 days thereafter. The starting dose was 20 ppm. A dose reduction schedule was followed: after 72 hours of treatment at 20 ppm, reducing to 10 ppm, and then reducing to 5 ppm on day 10. If an infant was extubated before 24 days, therapy was continued via nasal continuous positive airway pressure or nasal cannula to complete the protocol. 451 infants less than 30 weeks of gestation age were included in this trial, of which 449 were randomized and 2 were not randomized. There was a 1:1 randomization with 220 infants treated with placebo and 229 treated with inhaled nitric oxide.

It is believed that pre-term neonates that enrolled in and completed the BPD 301 study did not have pulmonary hypertension, since one of the exclusionary criteria was prior treatment with inhaled nitric oxide for any reason, and pulmonary hypertension in infants is routinely treated with inhaled nitric oxide. In order to enroll in the BPD 301 study and receive inhaled nitric oxide for the prevention of BPD, a pre-term neonate could not have already previously been administered inhaled nitric oxide. If a pre-term neonate exhibited at birth characteristics associated with pulmonary hypertension, he or she would have likely been treated with commercial inhaled nitric oxide, and if treated with commercial inhaled nitric oxide, he or she would not have been eligible for the study.

Additionally, if the pre-term neonate had undiagnosed pulmonary hypertension and happened to be placed on placebo (nitrogen) for purposes of the BPD-301 study, the pre-term neonate's hypoxic respiratory failure would have worsened and would have likely required immediate treatment with commercial inhaled nitric oxide. This administration of commercial inhaled nitric oxide would have failed the subject from the trial, both reducing the power of the trial and eliminating the subject from the study analysis.

A synopsis of the BPD-301 protocol follows.

Name of Sponsor/Company: INO Therapeutics LLC
Name of Investigational Product: INOmax ® (nitric oxide) for inhalation
Name of Active Ingredient: Nitric Oxide for Inhalation
Title of Study: Inhaled nitric oxide for the prevention of bronchopulmonary dysplasia (BPD) in preterm infants requiring mechanical ventilation or positive pressure support on days 5 to 14 after birth
Study center(s): Approximately 25
Studied period (years):                                                Phase of development: 3
Estimated date first subject enrolled: Dec. 30, 2009
Estimated date last subject completed: Aug. 2, 2012
Estimated end of follow up: Aug. 2, 2014

-continued

| Objectives: |
| Primary: |

The primary objective of this trial is to examine the efficacy of inhaled nitric oxide (iNO) in preterm infants <30 weeks gestational age (GA) and <1250 grams who require mechanical ventilation or positive pressure support on days 5 to 14 after birth.
Secondary:

The secondary objectives are to examine the safety of iNO on premature infants as measured by survival, adverse events, and outcomes at 18 months to 24 months of age, to evaluate the pharmacokinetics (PK) of iNO in preterm infants, and to measure the pharmacoeconomic (PE) impacts of iNO use on the management of preterm infants. Assessment will be:
To examine the safety of inhaled nitric oxide (iNO) on premature infants as measured by survival and adverse events.
To evaluate the pharmacokinetics (PK) of nitric oxide (NO) in preterm infants using plasma nitrite and nitrate (NOx) as surrogates
To evaluate the relationship between NOx and methemoglobin (MetHb)
To explore the relationship between NO exposure and clinical outcomes
To evaluate the economic implications of using nitric oxide for inhalation (iNO) to prevent BPD
Methodology:

Multi-center, double blind, placebo-controlled, randomized clinical trial. Infants who meet all enrollment criteria at any point during days 5 to 14 after birth will be randomized to inhaled NO starting at 20 ppm, or matching placebo, by means of a blinded INOvent ® delivery device. All infants will receive 24 days of therapy, following a dose reduction schedule. Infants who are extubated before 24 days will continue therapy via nasal continuous positive airway pressure (CPAP) or nasal cannula to complete 24 days' of therapy. The primary outcome measure will be survival without BPD at 36 weeks postmenstrual age using a physiologic assessment of BPD. Sparse pharmacokinetic (PK) samples will be collected from participating infants (3 samples each) on a randomized schedule. This study will include a 12 month and 18 to 24 month follow-up visits to assess safety and efficacy. All infants will be followed up to 18 to 24 months of corrected age for adverse events, somatic growth and neurologic development.
Number of subjects (planned): 450
Diagnosis and main criteria for inclusion:
Inclusion:
Preterm infants who are:

1. <1250 grams at birth
2. <30 weeks gestational age
3. 5 to 14 days of age (inclusive) at the time of entry
4. Requiring mechanical ventilation or for those infants ≤800 grams, positive pressure support (including CPAP) for primary respiratory insufficiency on days 5 to 14 days of age (inclusive)
Exclusion:

1. Preterm infants with life-threatening anomalies (cranial, cardiac, thoracic, chromosomal) or congenital diaphragmatic hernia with lung hypoplasia, or any subject who will not receive complete intensive care
2. Preterm infants with bilateral Grade 4 intraventricular hemorrhage (IVH)
3. Subjects who are dependent on right to left shunting to maintain the systemic circulation
4. Preterm infants who received prior iNO therapy
5. Use of another investigational agent
Investigational product, dosage and mode of administration: Nitric oxide for inhalation (or matching placebo) starting at 20 ppm (and following a dose reduction schedule) will be administered continuously into the inspiratory limb of the ventilator circuit in mechanically ventilated subject using a blinded version of the INOvent ® delivery system, or by nasal CPAP or nasal cannula, as needed to complete 24 days of therapy.
Duration of treatment: Study drug will be weaned from 20 ppm to 10 ppm after 72 hours of treatment. The next wean will be to 5 ppm on Day 10. If the infant deteriorates after any dose reduction, he/she may be put back on the previous treatment and weaning re-attempted as tolerated. Duration of treatment is 24 days.
Reference therapy, dosage and mode of administration: Placebo consisting of 100% Grade 5 Nitrogen ($N_2$) gas will be administered in a blinded manner identical to that of the active treatment.
Criteria for evaluation:
Efficacy:

Survival without BPD at 36 weeks postmenstrual age using a physiologic assessment
Severity of BPD (as defined by $FiO_2$ requirement at week 36) among survivors as determined by the level of support needed to remain $SaO_2$ ≥90%
Status at 40 and 44 weeks postmenstrual age
Hospitalization
Need for oxygen
Need for airway pressure support
Need for mechanical ventilation
Days of air pressure support for lung disease (birth hospitalization)
Days of hospitalization (birth hospitalization)
Use of postnatal corticosteroids for respiratory insufficiency (including dose and duration of therapy) (birth hospitalization)

Use of respiratory medications, oxygen, and days of all hospitalizations at 12 months and 18 to 24 months of corrected age.
Safety: Examine the safety of iNO in preterm infants at risk of BPD.
Incidence of methemoglobinemia and elevated nitrogen dioxide concentrations
Incidence and types of adverse events including:
Adverse events of interest will include intracranial hemorrhage of any type,
patent ductus arteriosus requiring intervention, necrotizing enterocolitis, intestinal perforations,
air leaks of any type, pulmonary hemorrhage, retinopathy of prematurity and sepsis of any type.
Incidence of death after 36 weeks postmenstrual to 12 month and 18 to 24 month of
corrected age, stratified by gestational age at birth.
Long-term neurodevelopmental outcome assessed by age appropriate developmental
assessments at 18 to 24 months of corrected age. Neurologic assessments at 18 to 24 months
will include the cognitive and language components of the Bayleys-3, a structured neurologic
examination, and a parental questionnaire.
Pharmacoeconomics (PE): Assessments of resource utilization will be made to determine if
INOmax therapy is cost effective or cost saving.
Pharmacokinetics (PK): Concentration data of NOx from sparse samples will be pooled to
evaluate the following PK parameters. Individual parameters may be estimated based on
simulated results. Demographic covariates may be evaluated using a population PK analysis
approach if sufficient data is available.
$C_{max}$: observed maximum plasma concentration
$T_{max}$: time at $C_{max}$
AUC: area under plasma concentration-time curve from 0 to last quantifiable time
point ($AUC_{0-t}$) and from 0 to infinity ($AUC_{0-inf}$)
$T_{1/2}$: terminal half-life
$V_{ss}$: volume of distribution at steady state
CL: total clearance
PK Analyses:

Linear correlation between NOx and MetHb will be evaluated.
Exposure-response relationship (PK vs. clinical outcomes) may be evaluated when
sufficient data available.
Statistical methods:

All efficacy analyses will be performed on an intent-to-treat (ITT) population that consists of all
randomized subjects. Safety analyses will be performed on a safety population that includes all
randomized subjects who receive study drug. The primary efficacy endpoint is survival without
BPD at 36 weeks GA. The primary method of analysis will use the generalized estimating
equation (GEE) for logistic regression. In addition, the Cochran-Mantel-Haenszel (CMH) test
will be performed to further evaluate the primary endpoint. For the secondary efficacy
endpoints, GEE for logistic regression will be used to analyze the binary response variables
and mixed-effects model with repeated-measures will be used to analyze continuous variables.
Additional statistical analyses will be performed using CMH test and van Elteren test as
appropriate. All statistical tests will be two-sided with a significance level of 0.05.

A safety analysis of the randomized population in the BPD-301 study revealed an unexpected anomalous finding in a subpopulation of white, male, preterm infants of less than 27 weeks. Data from this study indicate that white, male, preterm infants of less than 27 weeks gestational age are at significant risk of death when treated with inhaled nitric oxide for the prevention of BPD, as compared to placebo. The placebo and treatment groups were matched for the following characteristics: gestational age, age at the start of treatment, sex, length at birth, weight, head circumference, respiratory severity scores, apgar scores, and physical exam results. There were no anomalous findings to indicate that there was any particular reason, other than the inhaled nitric oxide itself, that caused this result.

The overall mortality rate in the trial was low. The mortality rate was not significantly different between inhaled nitric oxide and placebo groups (11.35% vs. 8.64%, p=0.436), evaluated with Fisher's exact test. See Table 1. Analysis of the mortality rates in different race groups demonstrated that, among the white population, the inhaled nitric oxide-treated pre-term infants had an unexpected higher mortality rate than those from the placebo group [Table 1].

TABLE 1

SUMMARY OF MORTALITY BY RACE

| | PLACEBO<br>N = 220<br>n (%) | INO<br>N = 229<br>n (%) | P-VALUE [1] |
|---|---|---|---|
| ALL | 19 (8.64%) | 26 (11.35%) | 0.436 |
| American Indian or Alaska Native | 1 (0.45%) | 0 (0.00%) | |
| Asian | 2 (0.91%) | 0 (0.00%) | |
| Black | 9 (4.09%) | 6 (2.62%) | |
| Hispanic | 4 (1.82%) | 3 (1.31%) | |
| Native Hawaiian or other Pacific Islander | 0 (0.00%) | 0 (0.00%) | |
| Other | 1 (0.45%) | 2 (0.87%) | |
| White | 2 (0.91%) | 15 (6.55%) | |

[1] Fisher's exact test.

In the subgroup of white preterm infants of less than 27 weeks, deaths were a statistically significant 15 (12.5%) for the treatment group versus only 2 (2.4%) in the placebo group [Tables 1 and 2]. There was no similar difference in mortality between treatment and placebo groups for any other racial category [Table 1].

TABLE 2

MORTALITY FOR WHITE PRETERM INFANTS
LESS THAN 27 WEEKS GESTATIONAL AGE

| ALIVE | PLACEBO<br>N = 84<br>n (%) | INO<br>N = 120<br>n (%) | P-VALUE [1] |
|---|---|---|---|
| Yes | 82 (97.6%) | 105 (87.5%) | 0.010 |
| No | 2 (2.4%) | 15 (12.5%) | |

[1] Fisher's exact test.

Additional analyses were performed to assess role of gender on mortality in the subset population of white infants less than 27 weeks gestational age. The mortality rate of the inhaled nitric oxide-treated white infants was significantly higher in the male group than in the female group (21.4% (3 of 15) vs. 4.7% (12 of 15), p=0.011) [Table 3]. All the white male infants that died were less than 27 weeks gestational age. One white male in the placebo group died and one white female in the placebo group died. Out of the 84 total placebo population, 37 were female and 47 were male. At the end of the study evaluation period, there was a highly statistically significant finding of death/mortality in the active/treatment arm as compared to the placebo. In sum, the BPD 301 trial unexpectedly identified an increased risk of mortality for white males less than 27 weeks gestational age, treated with inhaled nitric oxide for the prevention of BPD, than was shown in treated white females of the same gestational age. This gender discrepancy and unexpected mortality risk were not witnessed in other race groups.

TABLE 3

MORTALITY BY GENDER FOR INHALED NITRIC
OXIDE-TREATED WHITE INFANTS LESS
THAN 27 WEEKS GESTATIONAL AGE

| ALIVE | MALE<br>N = 56<br>n (%) | FEMALE<br>N = 64<br>n (%) | P-VALUE [1] |
|---|---|---|---|
| Yes | 44 (78.6%) | 61 (95.3%) | 0.011 |
| No | 12 (21.4%) | 3 (4.7%) | |

[1] Fisher's exact test.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the inventions herein have been described with reference to particular embodiments, it is to be understood that these embodiments are merely illustrative of the principles and applications of the present inventions. It will be apparent to those skilled in the art that various modifications and variations can be made to the methods and system of the present invention without departing from the spirit and scope of the inventions. Thus, it is intended that the present inventions include modifications and variations that are within the scope of the appended claims and their equivalents.

What is claimed is:

1. A method of treating a plurality of neonates of the same gestational age who are candidates for treatment with inhaled nitric oxide, wherein the plurality includes neonates of less than 27 weeks postmenstrual age who are not white, male neonates and at least one neonate who is a white, male neonate of less than 27 weeks postmenstrual age, the method comprising:
   (a) administering inhaled nitric oxide to each of the neonates of the plurality who is less than 27 weeks postmenstrual age and not a white, male neonate;
   (b) for each of the neonates of the plurality who is a white, male neonate of less than 27 weeks postmenstrual age, administering a treatment that includes one or more of ventilatory support, intravenous fluids, surfactant, and bicarbonate therapy, and does not initially include inhaled nitric oxide; and
   (c) withholding inhaled nitric oxide from each of the neonates of the plurality who is a white, male neonate of less than 27 weeks postmenstrual age until he reaches 27 weeks postmenstrual age; and, when he reaches 27 weeks postmenstrual age, beginning administration of inhaled nitric oxide to him,
   wherein each of the white, male neonates of less than 27 weeks postmenstrual age is excluded from inhaled nitric oxide treatment until he reaches 27 weeks postmenstrual age solely because he is a white, male neonate of less than 27 weeks postmenstrual age.

2. The method of claim 1, wherein the treatment of (b) administered to each of the neonates of the plurality who is a white male neonate of less than 27 weeks postmenstrual age comprises ventilatory support that includes supplemental oxygen.

3. The method of claim 2, wherein the ventilatory support comprises high-frequency oscillatory ventilation.

4. The method of claim 2, wherein the treatment of (b) administered to each of the white male neonates of less than 27 weeks postmenstrual age further comprises caffeine, vitamin A, or one or more surfactants.

5. The method of claim 1, wherein each of the white male neonates of less than 27 weeks postmenstrual age does not have left ventricular dysfunction and is not dependent on right-to-left shunting of blood.

* * * * *